US011234745B2

(12) United States Patent
Jackson

(10) Patent No.: US 11,234,745 B2
(45) Date of Patent: Feb. 1, 2022

(54) POLYAXIAL BONE SCREW ASSEMBLY WITH PARTIALLY SPHERICAL SCREW HEAD AND TWIST IN PLACE PRESSURE INSERT

(76) Inventor: Roger P. Jackson, Prairie Village, KS (US)

( * ) Notice: Subject to any disclaimer, the term of this patent is extended or adjusted under 35 U.S.C. 154(b) by 0 days.

(21) Appl. No.: 12/587,677

(22) Filed: Oct. 9, 2009

(65) Prior Publication Data

US 2010/0036433 A1 Feb. 11, 2010

Related U.S. Application Data

(63) Continuation-in-part of application No. 11/474,577, filed on Jun. 26, 2006, now Pat. No. 8,366,753.
(Continued)

(51) Int. Cl.
*A61B 17/68* (2006.01)
*A61B 17/86* (2006.01)
(Continued)

(52) U.S. Cl.
CPC ...... *A61B 17/8605* (2013.01); *A61B 17/7037* (2013.01); *A61B 17/863* (2013.01);
(Continued)

(58) Field of Classification Search
CPC ............. A61B 17/8605; A61B 17/7032; A61F 17/7001; A61F 17/7032; A61F 17/7035; A61F 17/7037; A61F 17/8605
See application file for complete search history.

(56) References Cited

U.S. PATENT DOCUMENTS

| | | | |
|---|---|---|---|
| 154,864 A | 9/1874 | Harvey | |
| 1,472,464 A | 10/1923 | Ellison | |

(Continued)

FOREIGN PATENT DOCUMENTS

| | | |
|---|---|---|
| DE | 19507141 | 9/1996 |
| DE | 29806563 | 6/1998 |

(Continued)

OTHER PUBLICATIONS

*EBI Omega 21 Brochure*, EBI Spine Systems, pub. 1999.
(Continued)

*Primary Examiner* — Christopher D. Prone
(74) *Attorney, Agent, or Firm* — Polsinelli PC

(57) ABSTRACT

A pivotal bone anchor assembly for a securing an elongate rod to a bone includes a shank having a capture portion and an anchor portion extending distally from the capture portion, and a receiver having an upper portion defining a receiver channel for receiving a rod and a base defining a cavity for receiving the shank capture portion. The assembly also includes a retainer configured to capture and hold the shank capture portion within the receiver cavity, as well as a pressure insert having a central drive tool opening and upright arms forming an insert channel. The pressure insert is loaded into a first position within the receiver channel with the insert channel in a non-alignment orientation with respect to the receiver channel, and then rotated about a longitudinal axis into a second position with the insert channel in alignment with the receiver channel.

27 Claims, 15 Drawing Sheets

Related U.S. Application Data

(60) Provisional application No. 60/699,092, filed on Jul. 14, 2005.

(51) Int. Cl.
*A61B 17/70* (2006.01)
*A61B 90/00* (2016.01)

(52) U.S. Cl.
CPC ....... *A61B 17/7011* (2013.01); *A61B 17/7032* (2013.01); *A61B 2090/037* (2016.02)

(56) References Cited

U.S. PATENT DOCUMENTS

| | | | |
|---|---|---|---|
| 1,646,143 A * | 10/1927 | Forster | F16J 9/20 |
| | | | 277/447 |
| 2,243,717 A | 5/1941 | Moreira | |
| 2,376,089 A * | 5/1945 | Savageau | F16B 33/00 |
| | | | 411/81 |
| 3,236,275 A | 2/1966 | Smith | |
| 3,444,775 A | 5/1969 | Hills | |
| 3,604,487 A | 9/1971 | Gilbert | |
| 3,989,284 A | 11/1976 | Blose | |
| 3,997,138 A | 12/1976 | Crock et al. | |
| 4,013,071 A | 3/1977 | Rosenberg | |
| 4,041,939 A | 8/1977 | Hall | |
| 4,190,091 A | 2/1980 | Colognori | |
| 4,347,845 A | 9/1982 | Mayfield | |
| 4,369,769 A | 1/1983 | Edwards | |
| 4,409,968 A | 10/1983 | Drummond | |
| 4,448,191 A | 5/1984 | Rodnyansky et al. | |
| 4,484,570 A | 11/1984 | Sutter et al. | |
| 4,600,225 A | 7/1986 | Blose | |
| 4,653,481 A | 3/1987 | Howland et al. | |
| 4,653,486 A | 3/1987 | Coker | |
| 4,743,260 A | 5/1988 | Burton | |
| 4,748,260 A | 5/1988 | Marlett | |
| 4,836,196 A | 6/1989 | Park et al. | |
| 4,877,020 A | 10/1989 | Vich | |
| 4,887,596 A | 12/1989 | Sherman | |
| 4,917,606 A | 4/1990 | Miller | |
| 4,946,458 A | 8/1990 | Harms et al. | |
| 4,950,269 A | 8/1990 | Gaines, Jr. | |
| 4,961,740 A | 10/1990 | Ray et al. | |
| 5,034,011 A | 7/1991 | Howland | |
| 5,067,428 A | 11/1991 | Dickerson et al. | |
| 5,084,048 A | 1/1992 | Jacob et al. | |
| 5,102,412 A | 4/1992 | Rogozinski | |
| 5,129,388 A | 7/1992 | Vignaud et al. | |
| 5,129,899 A | 7/1992 | Small et al. | |
| 5,147,363 A | 9/1992 | Harle | |
| 5,176,678 A | 1/1993 | Tsou | |
| 5,176,680 A | 1/1993 | Vignaud et al. | |
| 5,180,393 A | 1/1993 | Commarmond | |
| 5,201,734 A | 4/1993 | Cozad et al. | |
| 5,207,678 A | 5/1993 | Harms et al. | |
| 5,257,993 A | 11/1993 | Asher et al. | |
| 5,261,912 A | 11/1993 | Frigg | |
| 5,263,953 A | 11/1993 | Bagby | |
| 5,282,862 A | 2/1994 | Barker et al. | |
| 5,282,863 A | 2/1994 | Burton | |
| 5,306,275 A | 4/1994 | Bryan | |
| 5,312,404 A | 5/1994 | Asher et al. | |
| 5,330,472 A | 7/1994 | Metz-Stavenhagen | |
| 5,354,292 A | 10/1994 | Braeuer et al. | |
| 5,360,431 A | 11/1994 | Puno et al. | |
| 5,375,823 A | 12/1994 | Navas | |
| 5,387,211 A | 2/1995 | Saadatmanesh et al. | |
| 5,395,371 A | 3/1995 | Miller et al. | |
| 5,409,489 A | 4/1995 | Sioufi | |
| 5,415,661 A | 5/1995 | Holmes | |
| 5,423,816 A | 6/1995 | Lin | |
| 5,429,639 A | 7/1995 | Judet | |
| 5,434,001 A | 7/1995 | Yamada et al. | |
| 5,443,467 A * | 8/1995 | Biedermann et al. | 606/65 |
| 5,466,237 A | 11/1995 | Byrd, III et al. | |
| 5,468,241 A | 11/1995 | Metz-Stavenhagen et al. | |
| 5,474,551 A | 12/1995 | Finn et al. | |
| 5,474,555 A | 12/1995 | Puno et al. | |
| 5,476,462 A | 12/1995 | Allard et al. | |
| 5,476,464 A | 12/1995 | Metz-Stavenhagen et al. | |
| 5,480,401 A | 1/1996 | Navas | |
| 5,484,440 A | 1/1996 | Allard | |
| 5,489,307 A | 2/1996 | Kuslich et al. | |
| 5,490,750 A | 2/1996 | Gundy | |
| 5,496,321 A | 3/1996 | Puno et al. | |
| 5,501,684 A | 3/1996 | Schlapfer et al. | |
| 5,505,731 A | 4/1996 | Tornier | |
| 5,507,745 A | 4/1996 | Logroscino et al. | |
| 5,534,001 A | 7/1996 | Schlapfer et al. | |
| 5,540,688 A | 7/1996 | Navas | |
| 5,545,163 A | 8/1996 | Miller | |
| 5,549,607 A | 8/1996 | Olson et al. | |
| 5,549,608 A | 8/1996 | Errico et al. | |
| 5,554,157 A | 9/1996 | Errico et al. | |
| 5,562,660 A | 10/1996 | Grob | |
| 5,562,661 A | 10/1996 | Yoshimi et al. | |
| 5,569,247 A | 10/1996 | Morrison | |
| 5,569,251 A | 10/1996 | Baker et al. | |
| 5,578,033 A | 11/1996 | Errico et al. | |
| 5,584,834 A | 12/1996 | Errico et al. | |
| 5,586,984 A | 12/1996 | Errico et al. | |
| 5,591,166 A | 1/1997 | Bernhardt et al. | |
| 5,601,553 A | 2/1997 | Trebing et al. | |
| 5,605,458 A | 2/1997 | Bailey et al. | |
| 5,607,425 A | 3/1997 | Rogozinski | |
| 5,607,426 A | 3/1997 | Ralph et al. | |
| 5,607,428 A | 3/1997 | Lin | |
| 5,609,593 A | 3/1997 | Errico et al. | |
| 5,609,594 A | 3/1997 | Errico et al. | |
| 5,611,800 A | 3/1997 | Davis et al. | |
| 5,628,740 A | 5/1997 | Mullane | |
| 5,647,873 A | 7/1997 | Errico et al. | |
| 5,662,653 A | 9/1997 | Songer et al. | |
| 5,667,508 A | 9/1997 | Errico et al. | |
| 5,669,909 A | 9/1997 | Zdeblick et al. | |
| 5,669,911 A | 9/1997 | Errico et al. | |
| 5,672,175 A | 9/1997 | Martin | |
| 5,672,176 A * | 9/1997 | Biedermann | A61B 17/7032 |
| | | | 606/271 |
| 5,676,665 A | 10/1997 | Bryan | |
| 5,676,703 A | 10/1997 | Gelbard | |
| 5,681,319 A | 10/1997 | Biedermann et al. | |
| 5,683,391 A | 11/1997 | Boyd | |
| 5,690,630 A | 11/1997 | Errico et al. | |
| 5,702,393 A | 12/1997 | Pfaifer | |
| 5,711,709 A | 1/1998 | McCoy | |
| 5,716,356 A | 2/1998 | Biedermann et al. | |
| 5,720,751 A | 2/1998 | Jackson | |
| 5,723,013 A | 3/1998 | Jeanson et al. | |
| 5,725,528 A | 3/1998 | Errico et al. | |
| 5,728,098 A | 3/1998 | Sherman et al. | |
| 5,733,286 A | 3/1998 | Errico et al. | |
| 5,738,685 A | 4/1998 | Halm et al. | |
| 5,752,957 A | 5/1998 | Ralph et al. | |
| 5,782,833 A | 7/1998 | Haider | |
| 5,797,911 A | 8/1998 | Sherman et al. | |
| 5,800,435 A | 9/1998 | Errico et al. | |
| 5,817,094 A | 10/1998 | Errico et al. | |
| 5,863,293 A | 1/1999 | Richelsoph | |
| 5,876,402 A | 3/1999 | Errico et al. | |
| 5,879,350 A | 3/1999 | Sherman et al. | |
| 5,879,351 A | 3/1999 | Viart | |
| 5,882,350 A | 3/1999 | Ralph et al. | |
| 5,885,286 A | 3/1999 | Sherman et al. | |
| 5,891,145 A | 4/1999 | Morrison et al. | |
| 5,899,906 A | 5/1999 | Schenk | |
| RE36,221 E | 6/1999 | Breard et al. | |
| 5,910,141 A | 6/1999 | Morrison et al. | |
| 5,910,142 A | 6/1999 | Tatar | |
| 5,928,236 A | 7/1999 | Augagneur et al. | |
| 5,941,880 A | 8/1999 | Errico et al. | |
| 5,951,553 A | 9/1999 | Betz et al. | |
| 5,954,725 A | 9/1999 | Sherman et al. | |

(56) References Cited

U.S. PATENT DOCUMENTS

| | | |
|---|---|---|
| 5,961,517 A | 10/1999 | Biedermann et al. |
| 5,964,760 A | 10/1999 | Richelsoph |
| 5,964,767 A | 10/1999 | Tapia et al. |
| 5,997,539 A | 12/1999 | Errico et al. |
| 6,010,503 A | 1/2000 | Richelsoph et al. |
| 6,019,759 A | 2/2000 | Rogozinski |
| 6,022,350 A | 2/2000 | Ganem |
| 6,050,997 A | 4/2000 | Mullane |
| 6,053,917 A | 4/2000 | Sherman et al. |
| 6,063,088 A | 5/2000 | Winslow |
| 6,063,090 A * | 5/2000 | Schlapfer ............ 606/270 |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,110,172 A | 8/2000 | Jackson |
| 6,113,601 A | 9/2000 | Tatar |
| 6,129,763 A | 10/2000 | Chauvin et al. |
| 6,132,431 A | 10/2000 | Nilsson et al. |
| 6,132,432 A | 10/2000 | Richelsoph |
| 6,132,434 A | 10/2000 | Sherman et al. |
| 6,136,002 A | 10/2000 | Shih et al. |
| 6,136,003 A | 10/2000 | Hoeck et al. |
| 6,146,383 A | 11/2000 | Studer et al. |
| 6,162,223 A | 12/2000 | Orsak et al. |
| 6,168,597 B1 | 1/2001 | Biedermann et al. |
| 6,183,472 B1 | 2/2001 | Lutz |
| 6,187,005 B1 | 2/2001 | Brace et al. |
| 6,193,720 B1 | 2/2001 | Yuan et al. |
| 6,280,442 B1 | 3/2001 | Barker et al. |
| 6,280,445 B1 | 3/2001 | Morrison et al. |
| RE37,161 E | 5/2001 | Michelson et al. |
| 6,224,596 B1 | 5/2001 | Jackson |
| 6,224,598 B1 | 5/2001 | Jackson |
| 6,235,028 B1 | 5/2001 | Brumfield et al. |
| 6,241,730 B1 | 6/2001 | Alby |
| 6,241,731 B1 | 6/2001 | Fiz |
| 6,248,105 B1 | 6/2001 | Schlapfer et al. |
| 6,248,107 B1 | 6/2001 | Foley et al. |
| 6,251,112 B1 | 6/2001 | Jackson |
| 6,254,602 B1 | 7/2001 | Justis |
| 6,267,764 B1 | 7/2001 | Elberg |
| 6,267,765 B1 | 7/2001 | Taylor et al. |
| 6,273,888 B1 | 8/2001 | Justis |
| 6,287,308 B1 | 9/2001 | Betz et al. |
| 6,287,311 B1 | 9/2001 | Sherman et al. |
| 6,296,643 B1 | 10/2001 | Hopf et al. |
| 6,299,613 B1 | 10/2001 | Ogilvie et al. |
| 6,299,616 B1 | 10/2001 | Beger |
| 6,302,888 B1 | 10/2001 | Mellinger et al. |
| 6,309,391 B1 | 10/2001 | Crandall et al. |
| 6,328,739 B1 | 12/2001 | Liu et al. |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,379,356 B1 | 4/2002 | Jackson |
| 6,402,752 B2 | 6/2002 | Schaffler-Wachter et al. |
| 6,402,757 B1 | 6/2002 | Moore et al. |
| 6,440,133 B1 | 8/2002 | Beale et al. |
| 6,440,137 B1 | 8/2002 | Horvath et al. |
| 6,443,956 B1 | 9/2002 | Ray |
| 6,451,021 B1 | 9/2002 | Ralph et al. |
| 6,467,958 B1 | 10/2002 | Sasaki et al. |
| 6,471,703 B1 | 10/2002 | Ashman |
| 6,471,705 B1 | 10/2002 | Biedermann et al. |
| 6,478,797 B1 | 11/2002 | Paul |
| 6,478,798 B1 | 11/2002 | Howland |
| 6,485,491 B1 | 11/2002 | Farris et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,527,804 B1 | 3/2003 | Gauchet et al. |
| 6,530,929 B1 | 3/2003 | Jusis et al. |
| 6,533,786 B1 | 3/2003 | Needham et al. |
| 6,547,790 B2 | 4/2003 | Harkey, III et al. |
| 6,551,320 B2 | 4/2003 | Liebermann |
| 6,554,831 B1 | 4/2003 | Rivard et al. |
| 6,554,832 B2 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,565,567 B1 | 5/2003 | Haider |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,610,063 B2 | 8/2003 | Kumar et al. |
| 6,613,050 B1 | 9/2003 | Wagner et al. |
| 6,616,667 B1 | 9/2003 | Steiger et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,648,885 B1 | 11/2003 | Friesem |
| 6,648,887 B2 | 11/2003 | Ashman |
| 6,652,526 B1 | 11/2003 | Arafiles |
| 6,652,765 B1 | 11/2003 | Beaty |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Benlloch et al. |
| 6,679,833 B2 | 1/2004 | Smith et al. |
| 6,682,529 B2 | 1/2004 | Stahurski |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,743,231 B1 | 6/2004 | Gray et al. |
| 6,746,449 B2 | 6/2004 | Jones et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,778,861 B1 | 8/2004 | Liebrecht et al. |
| 6,780,186 B2 | 8/2004 | Errico et al. |
| 6,790,209 B2 | 9/2004 | Beale et al. |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,837,889 B2 | 1/2005 | Shluzas |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,932,817 B2 | 8/2005 | Baynham et al. |
| 6,945,972 B2 | 9/2005 | Frigg et al. |
| 6,953,462 B2 | 10/2005 | Liebermann |
| 6,955,677 B2 | 10/2005 | Dahners |

(56) References Cited

U.S. PATENT DOCUMENTS

| | | |
|---|---|---|
| 6,958,065 B2 | 10/2005 | Ueyama et al. |
| 6,964,664 B2 | 11/2005 | Freid et al. |
| 6,964,665 B2 | 11/2005 | Thomas et al. |
| 6,974,460 B2 | 12/2005 | Carbone et al. |
| 6,979,334 B2 | 12/2005 | Dalton |
| 6,981,973 B2 | 1/2006 | McKinley |
| 7,001,389 B1 | 2/2006 | Navarro et al. |
| RE39,035 E | 3/2006 | Finn et al. |
| 7,018,373 B2 | 3/2006 | Biedermann et al. |
| 7,018,379 B2 | 3/2006 | Drewry et al. |
| 7,141,051 B2 * | 11/2006 | Janowski ............ A61B 17/7032 606/272 |
| 7,250,052 B2 | 7/2007 | Landry et al. |
| 7,332,981 B2 | 1/2008 | Jackson |
| 7,513,905 B2 | 4/2009 | Jackson |
| 7,572,279 B2 | 8/2009 | Jackson |
| 7,625,396 B2 | 12/2009 | Jackson |
| 7,662,175 B2 | 2/2010 | Jackson |
| 7,776,067 B2 | 8/2010 | Jackson |
| 7,811,310 B2 | 10/2010 | Baker et al. |
| 7,833,250 B2 | 11/2010 | Jackson |
| 7,967,850 B2 | 6/2011 | Jackson |
| 8,137,386 B2 | 3/2012 | Jackson |
| 8,162,989 B2 | 4/2012 | Khalili |
| 8,192,440 B2 | 6/2012 | Jones et al. |
| 8,353,932 B2 | 1/2013 | Jackson |
| 8,377,102 B2 | 2/2013 | Jackson |
| 8,444,681 B2 | 5/2013 | Jackson et al. |
| 8,603,145 B2 | 12/2013 | Forton et al. |
| 8,696,711 B2 | 4/2014 | Jackson |
| 8,876,869 B1 | 11/2014 | Schafer et al. |
| 8,986,349 B1 | 3/2015 | German et al. |
| 9,066,762 B2 | 6/2015 | Jones |
| 9,144,444 B2 | 9/2015 | Jackson |
| 9,480,517 B2 | 11/2016 | Jackson et al. |
| 9,572,599 B1 | 2/2017 | Casey et al. |
| 9,788,866 B2 | 10/2017 | Jackson |
| 9,808,292 B2 | 11/2017 | Jackson |
| 9,895,172 B2 | 2/2018 | Biedermann et al. |
| 10,335,200 B2 | 7/2019 | Jackson |
| 10,456,173 B1 | 10/2019 | Casey et al. |
| 10,799,272 B2 | 10/2020 | Jackson |
| 2001/0001119 A1 | 5/2001 | Lombardo |
| 2001/0007941 A1 | 7/2001 | Steiner et al. |
| 2001/0010000 A1 | 7/2001 | Gertzbein et al. |
| 2001/0011172 A1 | 8/2001 | Orbay et al. |
| 2001/0012937 A1 | 8/2001 | Schaffler-Wachter et al. |
| 2001/0023350 A1 | 9/2001 | Choi |
| 2001/0037111 A1 | 11/2001 | Dixon et al. |
| 2001/0041894 A1 | 11/2001 | Campbell et al. |
| 2001/0047173 A1 | 11/2001 | Schlapfer et al. |
| 2001/0047174 A1 | 11/2001 | Donno et al. |
| 2001/0047175 A1 | 11/2001 | Doubler et al. |
| 2001/0052438 A1 | 12/2001 | Spencer |
| 2002/0004683 A1 | 1/2002 | Michelson |
| 2002/0007184 A1 | 1/2002 | Ogilvie et al. |
| 2002/0010467 A1 | 1/2002 | Cooper et al. |
| 2002/0013586 A1 | 1/2002 | Justis et al. |
| 2002/0016594 A1 | 2/2002 | Schlapfer et al. |
| 2002/0022764 A1 | 2/2002 | Smith et al. |
| 2002/0022842 A1 | 2/2002 | Horvath et al. |
| 2002/0026193 A1 * | 2/2002 | Barker et al. ................... 606/61 |
| 2002/0029040 A1 | 3/2002 | Morrison et al. |
| 2002/0035365 A1 | 3/2002 | Kumar et al. |
| 2002/0035366 A1 | 3/2002 | Walder et al. |
| 2002/0035367 A1 | 3/2002 | Ritland |
| 2002/0045898 A1 | 4/2002 | Freid et al. |
| 2002/0045899 A1 | 4/2002 | Errico et al. |
| 2002/0049446 A1 | 4/2002 | Harkey, III et al. |
| 2002/0055740 A1 | 5/2002 | Lieberman |
| 2002/0055741 A1 | 5/2002 | Schlapfer et al. |
| 2002/0058942 A1 | 5/2002 | Biedermann et al. |
| 2002/0068975 A1 | 5/2002 | Teitelbaum et al. |
| 2002/0072750 A1 | 6/2002 | Jackson |
| 2002/0082602 A1 | 6/2002 | Biedermann et al. |
| 2002/0082603 A1 | 6/2002 | Dixon et al. |
| 2002/0087159 A1 | 7/2002 | Thomas |
| 2002/0087161 A1 | 7/2002 | Randall et al. |
| 2002/0091386 A1 | 7/2002 | Martin et al. |
| 2002/0095153 A1 | 7/2002 | Jones et al. |
| 2002/0095154 A1 | 7/2002 | Atkinson et al. |
| 2002/0095881 A1 | 7/2002 | Shreiner |
| 2002/0103487 A1 | 8/2002 | Errico et al. |
| 2002/0111626 A1 | 8/2002 | Ralph et al. |
| 2002/0111627 A1 | 8/2002 | Vincent-Prestigiancomo |
| 2002/0116001 A1 | 8/2002 | Schaefer et al. |
| 2002/0120270 A1 | 8/2002 | Trieu et al. |
| 2002/0123752 A1 | 9/2002 | Schultheiss et al. |
| 2002/0133154 A1 | 9/2002 | Saint Martin |
| 2002/0133158 A1 | 9/2002 | Saint Martin |
| 2002/0138076 A1 | 9/2002 | Biedermann et al. |
| 2002/0138077 A1 | 9/2002 | Ferree |
| 2002/0203511 | 9/2002 | Wilson-MacDonald et al. |
| 2002/0143328 A1 | 10/2002 | Shluzas et al. |
| 2002/0143330 A1 | 10/2002 | Shluzas |
| 2002/0143332 A1 | 10/2002 | Lin et al. |
| 2002/0143338 A1 | 10/2002 | Orbay et al. |
| 2002/0143341 A1 | 10/2002 | Biedermann et al. |
| 2002/0161368 A1 | 10/2002 | Foley et al. |
| 2002/0161370 A1 | 10/2002 | Frigg et al. |
| 2002/0173789 A1 | 11/2002 | Howland |
| 2002/0173791 A1 | 11/2002 | Howland |
| 2002/0183747 A1 | 12/2002 | Jao et al. |
| 2002/0193794 A1 | 12/2002 | Taylor |
| 2002/0193795 A1 | 12/2002 | Gertzbein et al. |
| 2002/0198526 A1 | 12/2002 | Shaolian et al. |
| 2003/0004519 A1 | 1/2003 | Torode et al. |
| 2003/0023240 A1 | 1/2003 | Amrein et al. |
| 2003/0023243 A1 | 1/2003 | Biedermann et al. |
| 2003/0032957 A1 | 2/2003 | McKinley |
| 2003/0055426 A1 | 3/2003 | Carbone et al. |
| 2003/0055427 A1 | 3/2003 | Graf |
| 2003/0060826 A1 | 3/2003 | Foley et al. |
| 2003/0073995 A1 | 4/2003 | Reed |
| 2003/0073996 A1 | 4/2003 | Doubler et al. |
| 2003/0073998 A1 | 4/2003 | Pagliuca et al. |
| 2003/0078580 A1 | 4/2003 | Shitoto |
| 2003/0083657 A1 | 5/2003 | Drewry et al. |
| 2003/0083667 A1 | 5/2003 | Ralph et al. |
| 2003/0093077 A1 | 5/2003 | Schlapfer et al. |
| 2003/0093078 A1 | 5/2003 | Ritland |
| 2003/0100896 A1 | 5/2003 | Biedermann et al. |
| 2003/0100897 A1 | 5/2003 | Metz-Stavenhagen |
| 2003/0100904 A1 | 5/2003 | Biedermann |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0120275 A1 | 6/2003 | Lenke et al. |
| 2003/0125741 A1 | 7/2003 | Biedermann et al. |
| 2003/0125749 A1 | 7/2003 | Yuan et al. |
| 2003/0130659 A1 | 7/2003 | Haider |
| 2003/0130661 A1 | 7/2003 | Osman |
| 2003/0135210 A1 | 7/2003 | Dixon et al. |
| 2003/0135217 A1 | 7/2003 | Buttermann et al. |
| 2003/0139745 A1 | 7/2003 | Ashman |
| 2003/0149431 A1 | 8/2003 | Varieur |
| 2003/0149432 A1 | 8/2003 | Frigg et al. |
| 2003/0149435 A1 | 8/2003 | Baynham et al. |
| 2003/0153912 A1 | 8/2003 | Graf |
| 2003/0153920 A1 | 8/2003 | Ralph et al. |
| 2003/0163133 A1 | 8/2003 | Altarac et al. |
| 2003/0167058 A1 | 9/2003 | Shluzas |
| 2003/0171749 A1 | 9/2003 | Le Couedic et al. |
| 2003/0176862 A1 | 9/2003 | Taylor et al. |
| 2003/0176863 A1 | 9/2003 | Ueyama et al. |
| 2003/0181913 A1 | 9/2003 | Lieberman |
| 2003/0187433 A1 | 10/2003 | Lin |
| 2003/0187434 A1 * | 10/2003 | Lin ................................ 606/61 |
| 2003/0191470 A1 | 10/2003 | Ritland |
| 2003/0199872 A1 | 10/2003 | Markworth et al. |
| 2003/0199873 A1 | 10/2003 | Richelsoph |
| 2003/0208204 A1 | 11/2003 | Bailey et al. |
| 2003/0212398 A1 | 11/2003 | Jackson |
| 2003/0216735 A1 | 11/2003 | Altarac et al. |

(56) References Cited

U.S. PATENT DOCUMENTS

| | | |
|---|---|---|
| 2003/0220642 A1 | 11/2003 | Freudiger |
| 2003/0220643 A1 | 11/2003 | Ferree |
| 2003/0225408 A1 | 12/2003 | Nichols et al. |
| 2003/0229345 A1 | 12/2003 | Stahurski |
| 2003/0229347 A1 | 12/2003 | Sherman et al. |
| 2003/0236529 A1 | 12/2003 | Shluzas et al. |
| 2004/0006342 A1 | 1/2004 | Altarac et al. |
| 2004/0039383 A1 | 2/2004 | Jackson |
| 2004/0039384 A1 | 2/2004 | Boehm, Jr. et al. |
| 2004/0039385 A1 | 2/2004 | Mazda et al. |
| 2004/0049189 A1 | 3/2004 | Le Couedic et al. |
| 2004/0049190 A1 | 3/2004 | Biedermann et al. |
| 2004/0220671 A1 | 3/2004 | Ralph et al. |
| 2004/0073215 A1 | 4/2004 | Carli |
| 2004/0073218 A1 | 4/2004 | Dahners |
| 2004/0078051 A1 | 4/2004 | Davison et al. |
| 2004/0078082 A1 | 4/2004 | Lange |
| 2004/0087949 A1 | 5/2004 | Bono et al. |
| 2004/0087950 A1 | 5/2004 | Teitelbaum |
| 2004/0087952 A1 | 5/2004 | Borgstrom et al. |
| 2004/0092934 A1 | 5/2004 | Howland |
| 2004/0092938 A1 | 5/2004 | Carli |
| 2004/0097933 A1 | 5/2004 | Lourdel et al. |
| 2004/0106925 A1 | 6/2004 | Culbert |
| 2004/0111091 A1 | 6/2004 | Ogilvie et al. |
| 2004/0116929 A1 | 6/2004 | Barker et al. |
| 2004/0122442 A1 | 6/2004 | Lewis |
| 2004/0127904 A1 | 7/2004 | Konieczynski et al. |
| 2004/0133207 A1 | 7/2004 | Abdou |
| 2004/0138660 A1 | 7/2004 | Serhan |
| 2004/0138662 A1 | 7/2004 | Landry et al. |
| 2004/0143265 A1 | 7/2004 | Landry et al. |
| 2004/0147929 A1 | 7/2004 | Biedermann et al. |
| 2004/0147937 A1 | 7/2004 | Dunbar, Jr. et al. |
| 2004/0153068 A1* | 8/2004 | Janowski et al. ............... 606/61 |
| 2004/0158245 A1 | 8/2004 | Chin |
| 2004/0158247 A1 | 8/2004 | Sitiso et al. |
| 2004/0158258 A1 | 8/2004 | Bonati et al. |
| 2004/0167523 A1 | 8/2004 | Jackson |
| 2004/0167525 A1 | 8/2004 | Jackson |
| 2004/0172022 A1 | 9/2004 | Landry et al. |
| 2004/0172025 A1 | 9/2004 | Drewry et al. |
| 2004/0172031 A1 | 9/2004 | Rubecamp et al. |
| 2004/0176766 A1 | 9/2004 | Shluzas |
| 2004/0176776 A1 | 9/2004 | Zubok et al. |
| 2004/0186473 A1 | 9/2004 | Cournoyer et al. |
| 2004/0186474 A1 | 9/2004 | Matthis et al. |
| 2004/0186475 A1 | 9/2004 | Falahee |
| 2004/0210216 A1 | 10/2004 | Farris et al. |
| 2004/0210227 A1 | 10/2004 | Trail et al. |
| 2004/0215190 A1 | 10/2004 | Nguyen et al. |
| 2004/0215191 A1 | 10/2004 | Kitchen |
| 2004/0220567 A1 | 11/2004 | Eisermann et al. |
| 2004/0225289 A1 | 11/2004 | Biedermann et al. |
| 2004/0230100 A1 | 11/2004 | Shluzas |
| 2004/0236327 A1 | 11/2004 | Paul et al. |
| 2004/0236328 A1 | 11/2004 | Paul et al. |
| 2004/0236330 A1 | 11/2004 | Purcell et al. |
| 2004/0249378 A1 | 12/2004 | Saint Martin et al. |
| 2004/0249380 A1 | 12/2004 | Glascott |
| 2004/0254574 A1 | 12/2004 | Morrison et al. |
| 2004/0260283 A1 | 12/2004 | Wu et al. |
| 2004/0267264 A1 | 12/2004 | Konieczynski et al. |
| 2005/0010219 A1 | 1/2005 | Dalton |
| 2005/0027296 A1 | 2/2005 | Thramann et al. |
| 2005/0033298 A1 | 2/2005 | Hawkes et al. |
| 2005/0033436 A1 | 2/2005 | Schlapfer et al. |
| 2005/0033439 A1 | 2/2005 | Gordon et al. |
| 2005/0038430 A1 | 2/2005 | McKinley |
| 2005/0038432 A1 | 2/2005 | Shaolian et al. |
| 2005/0038433 A1 | 2/2005 | Young |
| 2005/0049588 A1 | 3/2005 | Jackson |
| 2005/0055026 A1 | 3/2005 | Biedermann et al. |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070899 A1 | 3/2005 | Doubler et al. |
| 2005/0070901 A1 | 3/2005 | David |
| 2005/0080415 A1 | 4/2005 | Keyer et al. |
| 2005/0085812 A1 | 4/2005 | Sherman et al. |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0090821 A1 | 4/2005 | Berrevoets et al. |
| 2005/0096652 A1 | 5/2005 | Burton |
| 2005/0107788 A1 | 5/2005 | Beaurain et al. |
| 2005/0113927 A1 | 5/2005 | Malek |
| 2005/0119658 A1 | 6/2005 | Ralph et al. |
| 2005/0124991 A1 | 6/2005 | Jahng |
| 2005/0131404 A1 | 6/2005 | Mazda et al. |
| 2005/0131405 A1 | 6/2005 | Molz, IV et al. |
| 2005/0131406 A1 | 6/2005 | Reiley et al. |
| 2005/0131407 A1 | 6/2005 | Sicvol et al. |
| 2005/0131408 A1 | 6/2005 | Sicvol et al. |
| 2005/0131413 A1 | 6/2005 | O'Driscoll et al. |
| 2005/0131419 A1 | 6/2005 | McCord et al. |
| 2005/0131422 A1 | 6/2005 | Anderson |
| 2005/0137594 A1 | 6/2005 | Doubler et al. |
| 2005/0137597 A1 | 6/2005 | Butler et al. |
| 2005/0141986 A1 | 6/2005 | Flesher |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149023 A1 | 7/2005 | Ritland |
| 2005/0149053 A1 | 7/2005 | Varieur |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0171543 A1 | 8/2005 | Timm et al. |
| 2005/0177154 A1 | 8/2005 | Moumene et al. |
| 2005/0177166 A1 | 8/2005 | Timm et al. |
| 2005/0182401 A1 | 8/2005 | Timm et al. |
| 2005/0182410 A1 | 8/2005 | Jackson |
| 2005/0187548 A1 | 8/2005 | Butler et al. |
| 2005/0187555 A1 | 8/2005 | Biedermann et al. |
| 2005/0192571 A1 | 9/2005 | Abdelgany |
| 2005/0192572 A1 | 9/2005 | Abdelgany et al. |
| 2005/0192573 A1 | 9/2005 | Abdelgany et al. |
| 2005/0192579 A1 | 9/2005 | Jackson |
| 2005/0192580 A1 | 9/2005 | Dalton |
| 2005/0192589 A1 | 9/2005 | Raymond et al. |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203518 A1 | 9/2005 | Biederman et al. |
| 2005/0203519 A1 | 9/2005 | Harms et al. |
| 2005/0215999 A1 | 9/2005 | Birkmeyer et al. |
| 2005/0216000 A1 | 9/2005 | Colleran et al. |
| 2005/0216001 A1 | 9/2005 | David |
| 2005/0216003 A1 | 9/2005 | Beidermann et al. |
| 2005/0228326 A1 | 10/2005 | Kalfas et al. |
| 2005/0228379 A1 | 10/2005 | Jackson |
| 2005/0228385 A1 | 10/2005 | Lee et al. |
| 2005/0228400 A1 | 10/2005 | Chao |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234459 A1 | 10/2005 | Falahee et al. |
| 2005/0240180 A1 | 10/2005 | Vienney |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251139 A1 | 11/2005 | Roh |
| 2005/0251140 A1 | 11/2005 | Shaolian et al. |
| 2005/0251141 A1 | 11/2005 | Frigg et al. |
| 2005/0261687 A1 | 11/2005 | Garamszegi et al. |

(56) References Cited

U.S. PATENT DOCUMENTS

| | | |
|---|---|---|
| 2005/0267470 A1 | 12/2005 | McBride |
| 2005/0267471 A1 | 12/2005 | Biedermann et al. |
| 2005/0267472 A1 | 12/2005 | Biedermann et al. |
| 2005/0267474 A1 | 12/2005 | Dalton |
| 2005/0267477 A1 | 12/2005 | Jackson |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1* | 12/2005 | Boschert ............ A61B 17/7037 606/328 |
| 2005/0277931 A1 | 12/2005 | Sweeney et al. |
| 2005/0277934 A1 | 12/2005 | Vardiman |
| 2005/0278023 A1 | 12/2005 | Zwirkoski |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009767 A1 | 1/2006 | Kiester |
| 2006/0009769 A1 | 1/2006 | Liebermann |
| 2006/0009770 A1 | 1/2006 | Speirs et al. |
| 2006/0009780 A1 | 1/2006 | Foley et al. |
| 2006/0015099 A1 | 1/2006 | Cannon et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0025771 A1 | 2/2006 | Jackson |
| 2006/0030850 A1 | 2/2006 | Keegan et al. |
| 2006/0036240 A1 | 2/2006 | Colleran et al. |
| 2006/0036242 A1 | 2/2006 | Nilsson et al. |
| 2006/0036243 A1 | 2/2006 | Sasso et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036254 A1 | 2/2006 | Lim |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg et al. |
| 2006/0074418 A1 | 4/2006 | Jackson |
| 2006/0079896 A1 | 4/2006 | Kwak et al. |
| 2006/0079898 A1 | 4/2006 | Ainsworth |
| 2006/0084977 A1 | 4/2006 | Liberman |
| 2006/0084980 A1 | 4/2006 | Melkent et al. |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0089645 A1 | 4/2006 | Eckman |
| 2006/0095035 A1 | 5/2006 | Jones et al. |
| 2006/0095038 A1 | 5/2006 | Jackson |
| 2006/0100622 A1 | 5/2006 | Jackson |
| 2006/0106381 A1 | 5/2006 | Ferree et al. |
| 2006/0106394 A1 | 5/2006 | Colleran |
| 2006/0111713 A1 | 5/2006 | Jackson |
| 2006/0111715 A1 | 5/2006 | Jackson |
| 2006/0122597 A1 | 6/2006 | Jones et al. |
| 2006/0122599 A1 | 6/2006 | Drewry et al. |
| 2006/0129239 A1 | 6/2006 | Kwak |
| 2006/0131421 A1 | 6/2006 | Dunn et al. |
| 2006/0142758 A1 | 6/2006 | Petit |
| 2006/0142760 A1 | 6/2006 | McDonnell |
| 2006/0149228 A1 | 7/2006 | Schlapfer et al. |
| 2006/0149229 A1 | 7/2006 | Kwak et al. |
| 2006/0149238 A1 | 7/2006 | Sherman et al. |
| 2006/0149240 A1 | 7/2006 | Jackson |
| 2006/0149251 A1 | 7/2006 | Ziolo et al. |
| 2006/0167454 A1 | 7/2006 | Ludwig et al. |
| 2006/0173454 A1 | 8/2006 | Spitler et al. |
| 2006/0173456 A1 | 8/2006 | Hawkes |
| 2006/0184171 A1 | 8/2006 | Biedermann |
| 2006/0184180 A1 | 8/2006 | Augostino |
| 2006/0189983 A1 | 8/2006 | Fallin et al. |
| 2006/0189985 A1 | 8/2006 | Lewis |
| 2006/0195090 A1 | 8/2006 | Suddaby |
| 2006/0195093 A1 | 8/2006 | Jahng |
| 2006/0200023 A1 | 9/2006 | Melkent et al. |
| 2006/0200130 A1 | 9/2006 | Hawkins et al. |
| 2006/0200132 A1 | 9/2006 | Chao et al. |
| 2006/0200133 A1 | 9/2006 | Jackson |
| 2006/0212033 A1 | 9/2006 | Rothman et al. |
| 2006/0217713 A1 | 9/2006 | Serhan et al. |
| 2006/0217716 A1 | 9/2006 | Baker |
| 2006/0217719 A1 | 9/2006 | Albert et al. |
| 2006/0229608 A1 | 10/2006 | Foster et al. |
| 2006/0229609 A1 | 10/2006 | Wang |
| 2006/0229613 A1 | 10/2006 | Timm |
| 2006/0241601 A1 | 10/2006 | Trautwein et al. |
| 2006/0247630 A1 | 11/2006 | Iott et al. |
| 2006/0247631 A1 | 11/2006 | Ahn et al. |
| 2006/0247632 A1 | 11/2006 | Winslow et al. |
| 2006/0247633 A1 | 11/2006 | Winslow et al. |
| 2006/0247658 A1 | 11/2006 | Pond, Jr. et al. |
| 2006/0260483 A1 | 11/2006 | Hartmann et al. |
| 2006/0264934 A1 | 11/2006 | Fallin |
| 2006/0264935 A1 | 11/2006 | White |
| 2006/0264962 A1 | 11/2006 | Chin et al. |
| 2006/0282075 A1 | 12/2006 | Labrom et al. |
| 2006/0282076 A1 | 12/2006 | Labrom et al. |
| 2006/0282077 A1 | 12/2006 | Labrom et al. |
| 2006/0282078 A1 | 12/2006 | Labrom et al. |
| 2006/0282079 A1 | 12/2006 | Labrom et al. |
| 2006/0282080 A1 | 12/2006 | Albert |
| 2006/0293657 A1 | 12/2006 | Hartmann |
| 2006/0293663 A1 | 12/2006 | Walkenhorst |
| 2006/0293664 A1 | 12/2006 | Schumacher |
| 2006/0293693 A1 | 12/2006 | Farr et al. |
| 2007/0005062 A1 | 1/2007 | Lange et al. |
| 2007/0005063 A1 | 1/2007 | Bruneau et al. |
| 2007/0005137 A1 | 1/2007 | Kwak |
| 2007/0016190 A1 | 1/2007 | Martinez et al. |
| 2007/0016194 A1 | 1/2007 | Shaolian et al. |
| 2007/0016200 A1 | 1/2007 | Jackson |
| 2007/0032123 A1 | 2/2007 | Timm et al. |
| 2007/0038219 A1 | 2/2007 | Matthis et al. |
| 2007/0043356 A1 | 2/2007 | Timm et al. |
| 2007/0049931 A1 | 3/2007 | Justis et al. |
| 2007/0049936 A1 | 3/2007 | Colleran et al. |
| 2007/0055236 A1 | 3/2007 | Hudgins et al. |
| 2007/0073289 A1 | 3/2007 | Kwak et al. |
| 2007/0073290 A1 | 3/2007 | Boehm, Jr. |
| 2007/0073291 A1 | 3/2007 | Cordaro et al. |
| 2007/0073293 A1 | 3/2007 | Martz et al. |
| 2007/0073294 A1 | 3/2007 | Chin et al. |
| 2007/0078461 A1 | 4/2007 | Shluzas |
| 2007/0088359 A1 | 4/2007 | Woods et al. |

(56) References Cited

U.S. PATENT DOCUMENTS

| | | |
|---|---|---|
| 2007/0090238 A1 | 4/2007 | Justis |
| 2007/0093813 A1 | 4/2007 | Callahan et al. |
| 2007/0093814 A1 | 4/2007 | Callahan, II et al. |
| 2007/0093815 A1 | 4/2007 | Callahan, II et al. |
| 2007/0093824 A1 | 4/2007 | Hestad et al. |
| 2007/0093833 A1 | 4/2007 | Kuiper et al. |
| 2007/0118119 A1 | 5/2007 | Hestad |
| 2007/0118122 A1 | 5/2007 | Butler et al. |
| 2007/0156142 A1 | 7/2007 | Rezach et al. |
| 2007/0161991 A1 | 7/2007 | Altarac et al. |
| 2007/0161997 A1 | 7/2007 | Thramann et al. |
| 2007/0161999 A1 | 7/2007 | Biedermann et al. |
| 2007/0173818 A1 | 7/2007 | Hestad et al. |
| 2007/0173822 A1 | 7/2007 | Bruneau et al. |
| 2007/0173832 A1 | 7/2007 | Tebbe et al. |
| 2007/0191832 A1 | 8/2007 | Trieu |
| 2007/0191841 A1 | 8/2007 | Justis et al. |
| 2007/0191846 A1 | 8/2007 | Bruneau et al. |
| 2007/0213720 A1 | 9/2007 | Gordon et al. |
| 2007/0225708 A1 | 9/2007 | Biedermann et al. |
| 2007/0233073 A1 | 10/2007 | Wisnewski et al. |
| 2007/0233085 A1 | 10/2007 | Biedermann et al. |
| 2007/0233089 A1 | 10/2007 | Dipoto et al. |
| 2007/0233092 A1 | 10/2007 | Falahee |
| 2007/0233094 A1 | 10/2007 | Colleran et al. |
| 2007/0233095 A1 | 10/2007 | Schlapfer |
| 2007/0233155 A1 | 10/2007 | Lovell |
| 2007/0244481 A1 | 10/2007 | Timm |
| 2007/0244482 A1 | 10/2007 | Aferzon |
| 2007/0270821 A1 | 11/2007 | Trieu et al. |
| 2007/0270836 A1 | 11/2007 | Bruneau et al. |
| 2007/0270837 A1 | 11/2007 | Eckhardt et al. |
| 2007/0270838 A1 | 11/2007 | Bruneau et al. |
| 2007/0270843 A1 | 11/2007 | Matthis et al. |
| 2007/0270869 A1 | 11/2007 | Young et al. |
| 2007/0276371 A1 | 11/2007 | Baynham et al. |
| 2007/0276379 A1 | 11/2007 | Miller et al. |
| 2007/0276380 A1 | 11/2007 | Jahng et al. |
| 2007/0288012 A1 | 12/2007 | Colleran et al. |
| 2007/0293862 A1 | 12/2007 | Jackson |
| 2008/0009862 A1 | 1/2008 | Hoffman |
| 2008/0015580 A1 | 1/2008 | Chao |
| 2008/0015597 A1 | 1/2008 | Whipple |
| 2008/0021465 A1 | 1/2008 | Shadduck et al. |
| 2008/0045953 A1 | 2/2008 | Garamszegi |
| 2008/0051787 A1 | 2/2008 | Remington et al. |
| 2008/0065071 A1 | 3/2008 | Park |
| 2008/0065079 A1 | 3/2008 | Bruneau et al. |
| 2008/0077136 A1 | 3/2008 | Triplett et al. |
| 2008/0077138 A1 | 3/2008 | Cohen et al. |
| 2008/0077143 A1 | 3/2008 | Shluzas |
| 2008/0086132 A1 | 4/2008 | Biedermann et al. |
| 2008/0091213 A1 | 4/2008 | Jackson |
| 2008/0103502 A1 | 5/2008 | Capote et al. |
| 2008/0114362 A1 | 5/2008 | Justis et al. |
| 2008/0114403 A1 | 5/2008 | Kuester et al. |
| 2008/0114404 A1 | 5/2008 | Matthis et al. |
| 2008/0119849 A1 | 5/2008 | Beardsley et al. |
| 2008/0119857 A1 | 5/2008 | Potash et al. |
| 2008/0125777 A1 | 5/2008 | Veldman et al. |
| 2008/0125787 A1 | 5/2008 | Doubler et al. |
| 2008/0125813 A1 | 5/2008 | Erickson et al. |
| 2008/0132957 A1 | 6/2008 | Matthis et al. |
| 2008/0140076 A1 | 6/2008 | Jackson |
| 2008/0140133 A1 | 6/2008 | Allard et al. |
| 2008/0140136 A1 | 6/2008 | Jackson |
| 2008/0147121 A1 | 6/2008 | Justis et al. |
| 2008/0147122 A1 | 6/2008 | Jackson |
| 2008/0147129 A1 | 6/2008 | Biedermann et al. |
| 2008/0147195 A1 | 6/2008 | Kwak et al. |
| 2008/0154279 A1 | 6/2008 | Schumaker et al. |
| 2008/0154315 A1 | 6/2008 | Jackson |
| 2008/0161857 A1 | 7/2008 | Hestad et al. |
| 2008/0167687 A1 | 7/2008 | Colleran et al. |
| 2008/0172090 A1 | 7/2008 | Molz |
| 2008/0172091 A1 | 7/2008 | Anderson |
| 2008/0172096 A1 | 7/2008 | Hawkins |
| 2008/0177316 A1 | 7/2008 | Bergeron et al. |
| 2008/0177317 A1 | 7/2008 | Jackson |
| 2008/0177323 A1 | 7/2008 | Null et al. |
| 2008/0177388 A1 | 7/2008 | Patterson et al. |
| 2008/0183212 A1 | 7/2008 | Veldman et al. |
| 2008/0183213 A1 | 7/2008 | Veldman et al. |
| 2008/0183216 A1 | 7/2008 | Jackson |
| 2008/0183219 A1 | 7/2008 | Jackson |
| 2008/0188898 A1 | 8/2008 | Jackson |
| 2008/0195153 A1 | 8/2008 | Thompson |
| 2008/0195155 A1 | 8/2008 | Hoffman et al. |
| 2008/0200918 A1 | 8/2008 | Spitler et al. |
| 2008/0215100 A1 | 9/2008 | Matthis et al. |
| 2008/0221681 A1 | 9/2008 | Trieu et al. |
| 2008/0228184 A1 | 9/2008 | Hestad |
| 2008/0228228 A1 | 9/2008 | Hestad et al. |
| 2008/0234736 A1 | 9/2008 | Trieu et al. |
| 2008/0234737 A1 | 9/2008 | Boschert |
| 2008/0234738 A1 | 9/2008 | Zylber et al. |
| 2008/0234739 A1 | 9/2008 | Hudgins et al. |
| 2008/0234744 A1 | 9/2008 | Zylber et al. |
| 2008/0234761 A1 | 9/2008 | Jackson |
| 2008/0243052 A1 | 10/2008 | Pond et al. |
| 2008/0243185 A1 | 10/2008 | Felix et al. |
| 2008/0243193 A1 | 10/2008 | Ensign et al. |
| 2008/0262551 A1 | 10/2008 | Rice et al. |
| 2008/0262554 A1 | 10/2008 | Hayes et al. |
| 2008/0269804 A1 | 10/2008 | Holt |
| 2008/0269805 A1 | 10/2008 | Dekutoski et al. |
| 2008/0269809 A1 | 10/2008 | Garamszegi |
| 2008/0275456 A1 | 11/2008 | Vonwiller et al. |
| 2008/0275504 A1 | 11/2008 | Bonin et al. |
| 2008/0294203 A1 | 11/2008 | Kovach et al. |
| 2008/0300630 A1 | 12/2008 | Bonnema et al. |
| 2008/0300631 A1 | 12/2008 | Tornier |
| 2008/0300633 A1 | 12/2008 | Jackson |
| 2008/0306513 A1 | 12/2008 | Winslow et al. |
| 2008/0306525 A1 | 12/2008 | Winslow et al. |
| 2008/0306526 A1 | 12/2008 | Winslow et al. |
| 2008/0306536 A1 | 12/2008 | Frigg et al. |
| 2008/0306540 A1 | 12/2008 | Mitchell et al. |
| 2008/0306543 A1 | 12/2008 | Cain et al. |
| 2008/0312655 A1 | 12/2008 | Kirschman et al. |
| 2008/0312703 A1 | 12/2008 | Hestad et al. |
| 2008/0312704 A1 | 12/2008 | Hestad et al. |
| 2008/0319482 A1 | 12/2008 | Jackson |
| 2008/0319490 A1 | 12/2008 | Jackson |
| 2009/0018557 A1 | 1/2009 | Pisharodi |
| 2009/0018583 A1 | 1/2009 | Song et al. |
| 2009/0024165 A1 | 1/2009 | Ferree |
| 2009/0048601 A1 | 2/2009 | Forton et al. |
| 2009/0048631 A1 | 2/2009 | Bhatnagar et al. |
| 2009/0062866 A1 | 3/2009 | Jackson |
| 2009/0082666 A1 | 3/2009 | Geist et al. |
| 2009/0088803 A1 | 4/2009 | Justis et al. |
| 2009/0093820 A1 | 4/2009 | Trieu et al. |
| 2009/0093846 A1 | 4/2009 | Hestad et al. |
| 2009/0099606 A1 | 4/2009 | Hestad et al. |
| 2009/0099608 A1 | 4/2009 | Szczesny |
| 2009/0105820 A1 | 4/2009 | Jackson |
| 2009/0112265 A1 | 4/2009 | Hudgins et al. |
| 2009/0112266 A1 | 4/2009 | Weng et al. |
| 2009/0112269 A1 | 4/2009 | Lieberman et al. |
| 2009/0143828 A1 | 6/2009 | Stad et al. |
| 2009/0149885 A1 | 6/2009 | Durward et al. |
| 2009/0149892 A1 | 6/2009 | Stad et al. |
| 2009/0157120 A1 | 6/2009 | Marino et al. |
| 2009/0163901 A1 | 6/2009 | Fisher et al. |
| 2009/0163953 A1 | 6/2009 | Biedermann et al. |
| 2009/0163954 A1 | 6/2009 | Kwak |
| 2009/0171392 A1 | 7/2009 | Garcia-Bengochea et al. |
| 2009/0171395 A1 | 7/2009 | Jeon et al. |
| 2009/0177232 A1 | 7/2009 | Kiester |
| 2009/0177237 A1 | 7/2009 | Zucherman et al. |
| 2009/0182430 A1 | 7/2009 | Tyber et al. |
| 2009/0198281 A1 | 8/2009 | Rice et al. |
| 2009/0216278 A1 | 8/2009 | Song |

(56) References Cited

U.S. PATENT DOCUMENTS

| | | | |
|---|---|---|---|
| 2009/0221877 A1 | 9/2009 | Woods | |
| 2009/0228045 A1 | 9/2009 | Hayes et al. | |
| 2009/0240292 A1 | 9/2009 | Butler et al. | |
| 2009/0248077 A1 | 10/2009 | Johns | |
| 2009/0248083 A1 | 10/2009 | Patterson et al. | |
| 2010/0030280 A1 | 2/2010 | Jackson | |
| 2010/0087865 A1 | 4/2010 | Biedermann et al. | |
| 2011/0077694 A1 | 3/2011 | Biedermann et al. | |
| 2011/0213424 A1 | 9/2011 | Biedermann et al. | |
| 2011/0282399 A1 | 11/2011 | Jackson | |
| 2012/0165881 A1 | 6/2012 | Biedermann et al. | |
| 2012/0179210 A1 | 7/2012 | Garamszegi | |
| 2012/0265257 A1 | 10/2012 | Jackson | |
| 2012/0303070 A1 | 11/2012 | Jackson | |
| 2013/0060292 A1 | 3/2013 | Jackson | |
| 2013/0079830 A1 | 3/2013 | Garamszegi et al. | |
| 2013/0131730 A1 | 5/2013 | Jackson et al. | |
| 2013/0268006 A1 | 10/2013 | Garamszegi | |
| 2013/0345756 A1 | 12/2013 | Berrevoets et al. | |
| 2014/0135854 A1 | 5/2014 | Dec et al. | |
| 2014/0172018 A1 | 6/2014 | Gephart et al. | |
| 2014/0172023 A1 | 6/2014 | Garamszegi | |
| 2014/0379031 A1 | 12/2014 | Biedermann et al. | |
| 2015/0182260 A1 | 7/2015 | Jackson et al. | |
| 2016/0220280 A1 | 8/2016 | Jackson | |
| 2017/0189074 A1 | 7/2017 | Biedermann et al. | |
| 2017/0196610 A1 | 7/2017 | Jackson | |
| 2018/0021067 A1 | 1/2018 | Jackson | |
| 2018/0214182 A1 | 8/2018 | Jackson | |
| 2018/0235667 A1 | 8/2018 | Jackson | |
| 2019/0254718 A1 | 8/2019 | Jackson | |
| 2019/0282278 A1 | 9/2019 | Schlapfer et al. | |
| 2019/0365425 A1 | 12/2019 | Casey et al. | |
| 2020/0022738 A1 | 1/2020 | Jackson | |
| 2021/0022776 A1 | 1/2021 | Jackson | |
| 2021/0161564 A1 | 6/2021 | Jackson | |

FOREIGN PATENT DOCUMENTS

| | | |
|---|---|---|
| DE | 20207850 U1 | 10/2002 |
| DE | 102007055745 | 7/2008 |
| EP | 0172130 | 9/1986 |
| EP | 0195455 | 9/1986 |
| EP | 0667127 | 8/1995 |
| EP | 0669109 | 8/1995 |
| EP | 0677277 | 10/1995 |
| EP | 1121902 | 8/2001 |
| EP | 1190678 | 3/2002 |
| EP | 1570795 | 9/2005 |
| EP | 1579816 | 9/2005 |
| EP | 1634537 | 3/2006 |
| EP | 2082709 | 7/2009 |
| FR | 2715825 | 8/1995 |
| FR | 2717370 | 9/1995 |
| FR | 2718946 | 10/1995 |
| FR | 2729291 | 7/1996 |
| FR | 2796545 | 1/2001 |
| FR | 2799949 | 4/2001 |
| FR | 2814936 | 4/2002 |
| FR | 2815535 | 4/2002 |
| FR | 2856578 | 6/2003 |
| FR | 2865373 | 1/2004 |
| FR | 2865375 | 1/2004 |
| FR | 2865377 | 1/2004 |
| FR | 2846223 | 4/2004 |
| FR | 2857850 | 4/2004 |
| FR | 2865378 | 10/2004 |
| GB | 2365345 | 2/2002 |
| GB | 2382304 | 5/2003 |
| JP | S4867159 | 9/1973 |
| JP | S50106061 | 8/1975 |
| JP | H10277070 | 10/1998 |
| JP | 2000325358 | 3/2000 |
| JP | 2002052030 | 2/2002 |
| JP | 2002221218 | 8/2002 |
| SU | 371359 | 2/1973 |
| WO | 8909030 | 10/1989 |
| WO | 8912431 | 12/1989 |
| WO | 9116018 | 10/1991 |
| WO | 9116020 | 10/1991 |
| WO | 9321848 | 11/1993 |
| WO | 9325161 | 12/1993 |
| WO | 9428824 | 12/1994 |
| WO | 9513755 | 5/1995 |
| WO | WO 95/13755 | 5/1995 |
| WO | 9528889 | 11/1995 |
| WO | 9531947 | 11/1995 |
| WO | 9621396 | 7/1996 |
| WO | 9625104 | 8/1996 |
| WO | 9628105 | 9/1996 |
| WO | 9641582 | 12/1996 |
| WO | 9714368 | 4/1997 |
| WO | 9727812 | 8/1997 |
| WO | 9730649 | 8/1997 |
| WO | 9737604 | 10/1997 |
| WO | 9737605 | 10/1997 |
| WO | 9812977 | 4/1998 |
| WO | 9815233 | 4/1998 |
| WO | 9825534 | 6/1998 |
| WO | 9834554 | 8/1998 |
| WO | 9834556 | 8/1998 |
| WO | 9838924 | 9/1998 |
| WO | 9903415 | 1/1999 |
| WO | 9905980 | 2/1999 |
| WO | 9932084 | 7/1999 |
| WO | 9938463 | 8/1999 |
| WO | 9947083 | 9/1999 |
| WO | 9949802 | 10/1999 |
| WO | 2000015125 | 3/2000 |
| WO | 2000022997 | 4/2000 |
| WO | 2000027297 | 5/2000 |
| WO | 2000072769 | 7/2000 |
| WO | 2000065268 | 11/2000 |
| WO | 2000066045 | 11/2000 |
| WO | 2001006940 | 2/2001 |
| WO | 2001008574 | 2/2001 |
| WO | 2001010317 | 2/2001 |
| WO | 2001015612 | 3/2001 |
| WO | 2001022893 | 4/2001 |
| WO | 2001028435 | 4/2001 |
| WO | 2001028436 | 4/2001 |
| WO | 2001045576 | 6/2001 |
| WO | 2001049191 | 7/2001 |
| WO | 20010058370 | 8/2001 |
| WO | 2001067972 | 9/2001 |
| WO | 2001067974 | 9/2001 |
| WO | 2002022030 | 3/2002 |
| WO | 2002034150 | 5/2002 |
| WO | 2002054966 | 7/2002 |
| WO | WO02/054966 | 7/2002 |
| WO | 2002102259 | 12/2002 |
| WO | 2003007828 | 1/2003 |
| WO | 2003026523 | 4/2003 |
| WO | 2003037199 | 5/2003 |
| WO | 2003047442 | 6/2003 |
| WO | 2003068083 | 8/2003 |
| WO | 2003068088 | 8/2003 |
| WO | WO03/068088 | 8/2003 |
| WO | 2003084415 | 10/2003 |
| WO | 2003094699 | 11/2003 |
| WO | 2004022108 | 3/2004 |
| WO | WO2004/041100 | 5/2004 |
| WO | 2004075778 | 9/2004 |
| WO | WO2004/089245 | 10/2004 |
| WO | 2004098452 | 11/2004 |
| WO | 2004105577 | 12/2004 |
| WO | WO2004/107997 | 12/2004 |
| WO | WO2005/000136 | 1/2005 |
| WO | WO2005/000137 | 1/2005 |
| WO | 2005013839 | 2/2005 |
| WO | 2005018466 | 3/2005 |
| WO | 2005018471 | 3/2005 |
| WO | WO2005/020829 | 3/2005 |
| WO | 2005030068 | 4/2005 |

(56) References Cited

FOREIGN PATENT DOCUMENTS

| | | |
|---|---|---|
| WO | 2005065374 | 7/2005 |
| WO | WO2005/072632 | 8/2005 |
| WO | 2005087121 | 9/2005 |
| WO | WO2005/082262 | 9/2005 |
| WO | WO2005/099400 | 10/2005 |
| WO | 2005102195 | 11/2005 |
| WO | 2005104969 | 11/2005 |
| WO | 2006020530 | 2/2006 |
| WO | WO2006/012088 | 2/2006 |
| WO | WO2006/017616 | 2/2006 |
| WO | WO2006/028537 | 3/2006 |
| WO | 2006042188 | 4/2006 |
| WO | 2006047711 | 5/2006 |
| WO | 2006054111 | 5/2006 |
| WO | 2006065607 | 6/2006 |
| WO | 2006066685 | 6/2006 |
| WO | 2006068711 | 6/2006 |
| WO | 2006071742 | 7/2006 |
| WO | 2006079531 | 8/2006 |
| WO | 2006096240 | 9/2006 |
| WO | 2006096351 | 9/2006 |
| WO | 2006104874 | 10/2006 |
| WO | 2006110463 | 10/2006 |
| WO | 2006116437 | 11/2006 |
| WO | 2006119447 | 11/2006 |
| WO | 2007002409 | 1/2007 |
| WO | 2007038350 | 4/2007 |
| WO | 2007040750 | 4/2007 |
| WO | 2007040888 | 4/2007 |
| WO | 2007041702 | 4/2007 |
| WO | 2007053566 | 5/2007 |
| WO | 2007060534 | 5/2007 |
| WO | 2007075454 | 7/2007 |
| WO | 2007081849 | 8/2007 |
| WO | 2007087469 | 8/2007 |
| WO | 2007087628 | 8/2007 |
| WO | 2007090021 | 8/2007 |
| WO | 2007092056 | 8/2007 |
| WO | 2007092870 | 8/2007 |
| WO | 2007097905 | 8/2007 |
| WO | 2007109470 | 9/2007 |
| WO | 2007114834 | 10/2007 |
| WO | 2007121030 | 10/2007 |
| WO | 2007121057 | 10/2007 |
| WO | 2007121271 | 10/2007 |
| WO | 2007123920 | 11/2007 |
| WO | 2007124249 | 11/2007 |
| WO | 2007127595 | 11/2007 |
| WO | 2007127604 | 11/2007 |
| WO | 2007138270 | 12/2007 |
| WO | 2007146032 | 12/2007 |
| WO | 2008005740 | 1/2008 |
| WO | 2008006098 | 1/2008 |
| WO | 2008008511 | 1/2008 |
| WO | 2008013892 | 1/2008 |
| WO | 2008027860 | 3/2008 |
| WO | 2008033742 | 3/2008 |
| WO | 2008036975 | 3/2008 |
| WO | 2008037256 | 4/2008 |
| WO | 2008039777 | 4/2008 |
| WO | 2008042948 | 4/2008 |
| WO | 2008048923 | 4/2008 |
| WO | 2008048953 | 4/2008 |
| WO | 2008051737 | 5/2008 |
| WO | 2008069420 | 6/2008 |
| WO | 2008070716 | 6/2008 |
| WO | 2008134703 | 6/2008 |
| WO | 2008078163 | 7/2008 |
| WO | 2008082737 | 7/2008 |
| WO | 2008100590 | 8/2008 |
| WO | 2008118295 | 10/2008 |
| WO | 2008119006 | 10/2008 |
| WO | 2008124772 | 10/2008 |
| WO | 2008140756 | 11/2008 |
| WO | 2008157589 | 12/2008 |
| WO | 2009003153 | 12/2008 |
| WO | 2009006225 | 1/2009 |
| WO | 2009011845 | 1/2009 |
| WO | 2009014540 | 1/2009 |
| WO | 2009018086 | 2/2009 |
| WO | 2009029928 | 2/2009 |
| WO | 2009055028 | 4/2009 |
| WO | 2009055400 | 4/2009 |
| WO | 2009055407 | 4/2009 |

OTHER PUBLICATIONS

*Claris Instrumentation Brochure*, G Med, pub. 1997.
*CD Horizon M8 Multi Axial Screw Spinal System Brochure*, Medtronic Sofamor Danek, no publish date.
*Contour Spinal System Brochure*, Ortho Development, no publish date.
*Xia Spinal System Brochure*, Stryker Howmedica Osteonics, no publish date.
*The Rod Plate System Brochure*, Stryker Howmedica Osteonics, pub. Oct. 1999.
*Silhouette Spinal Fixation System Brochure*, Sulzer Medica Spine-Tech, no publish date.
*SDRS Surgical Dynamics Rod System Brochure*, Surgical Dynamics, pub. 1998-1999.
*Versalok Low Back Fixation System Brochure*, Wright Medical Technology, Inc., pub. 1997.
*The Strength of Innovation Advertisement*, Blackstone Medical Inc., no publish date.
*The Moss Miami 6.0mm System* Advertisement, author unknown, no publish date.
Brochure of Tyco/Healthcare/Surgical Dynamics on Spiral Radius 90D, Publication Date: Sep. 2001, pp. 1-8.
VLS System Variable Locking Screw Brochure, Interpore Cross International, 1999.
Brochure of DePuySpine on Surgical Technique, Published 2004, pp. 1-36.
European Search Report, EP14189707.4, dated Feb. 25, 2015.

\* cited by examiner

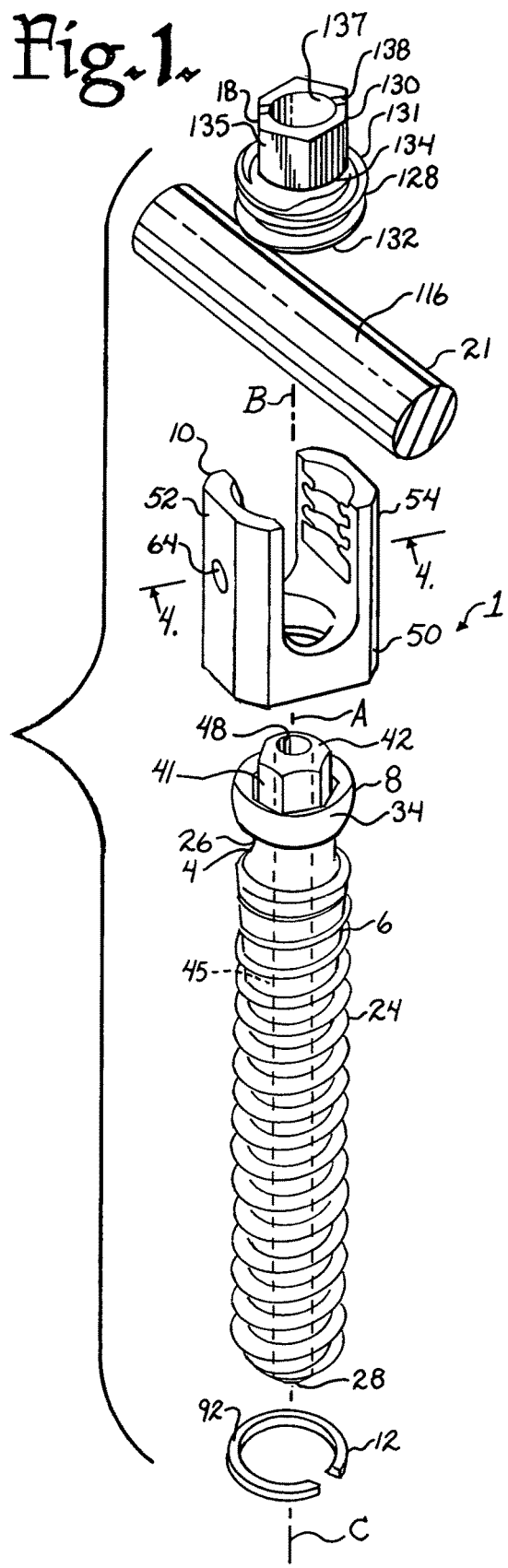
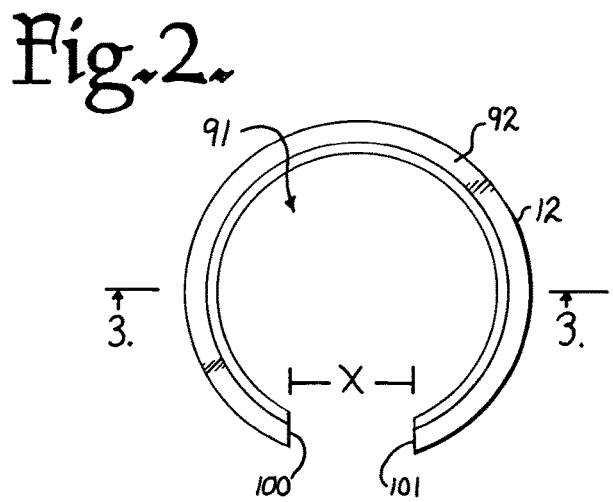
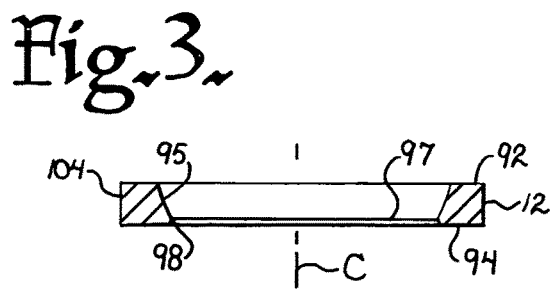
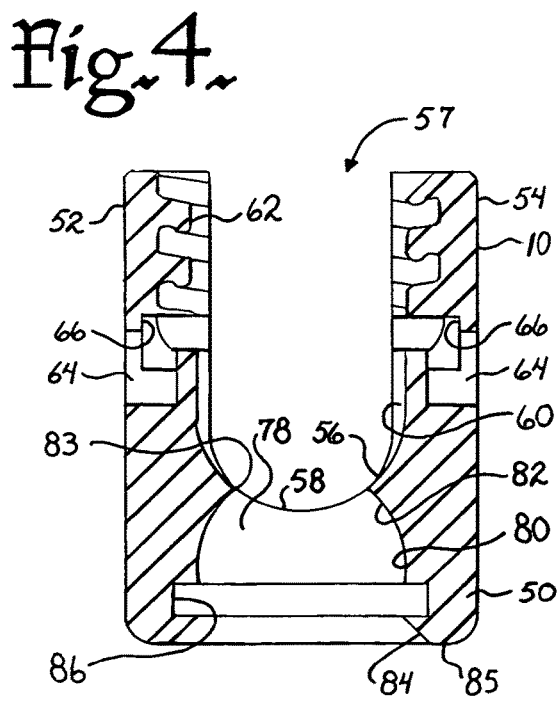

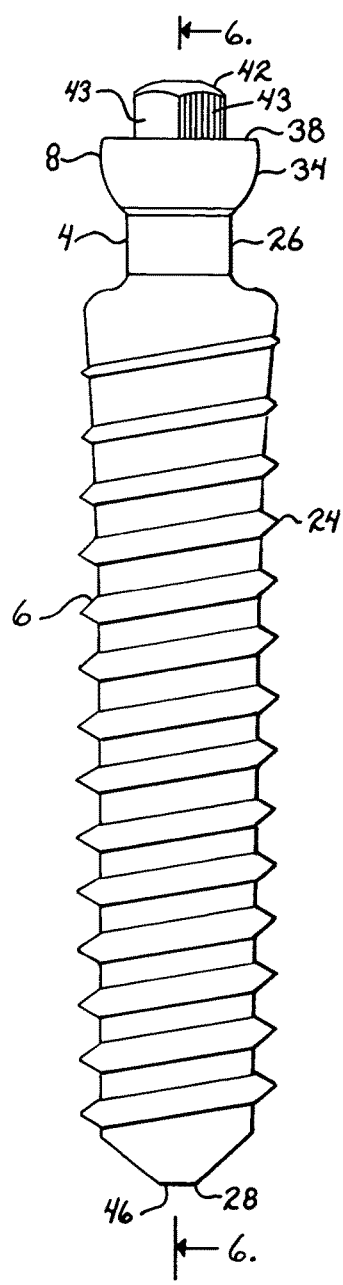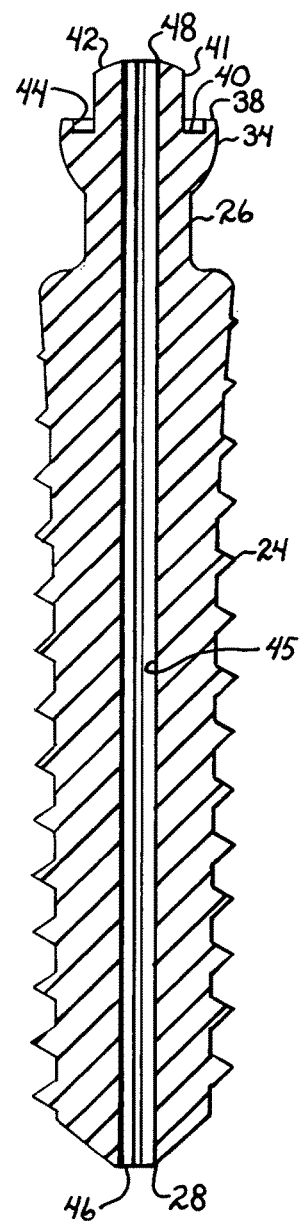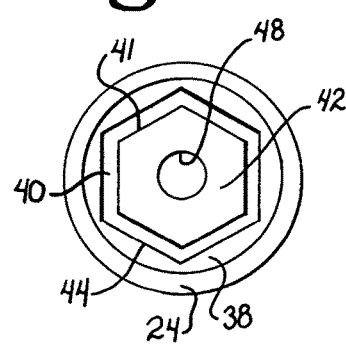

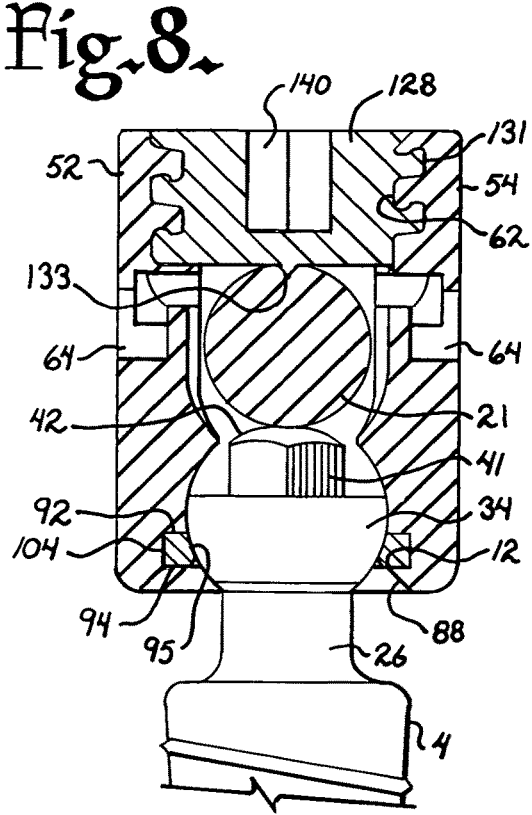
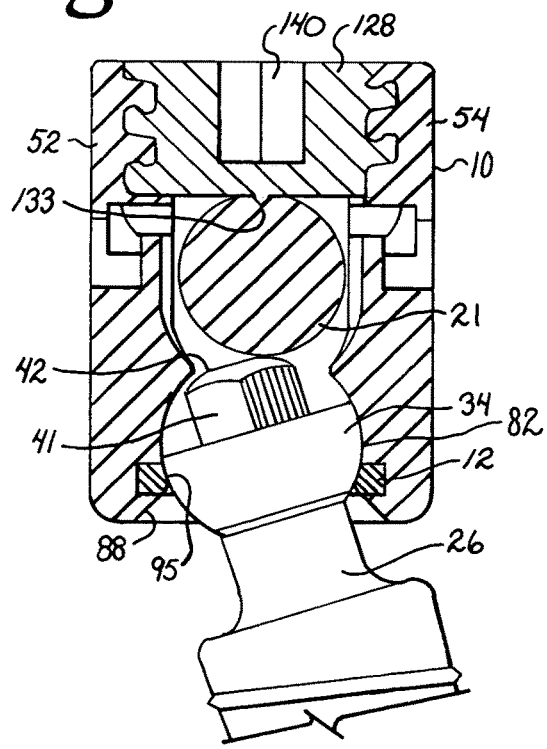
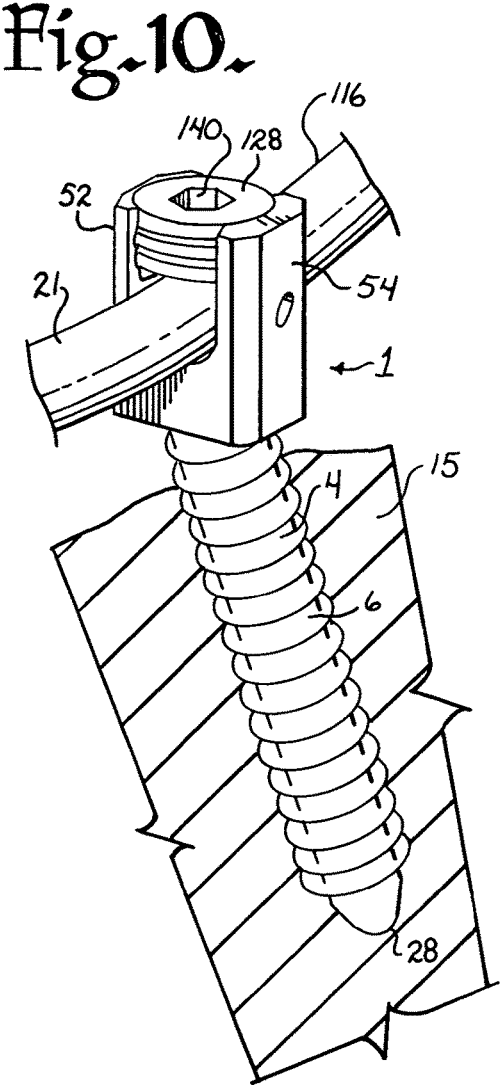

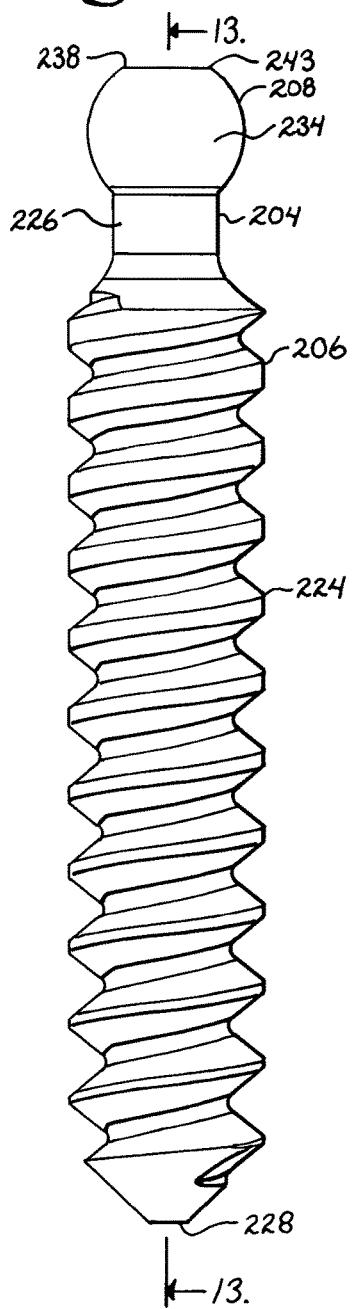
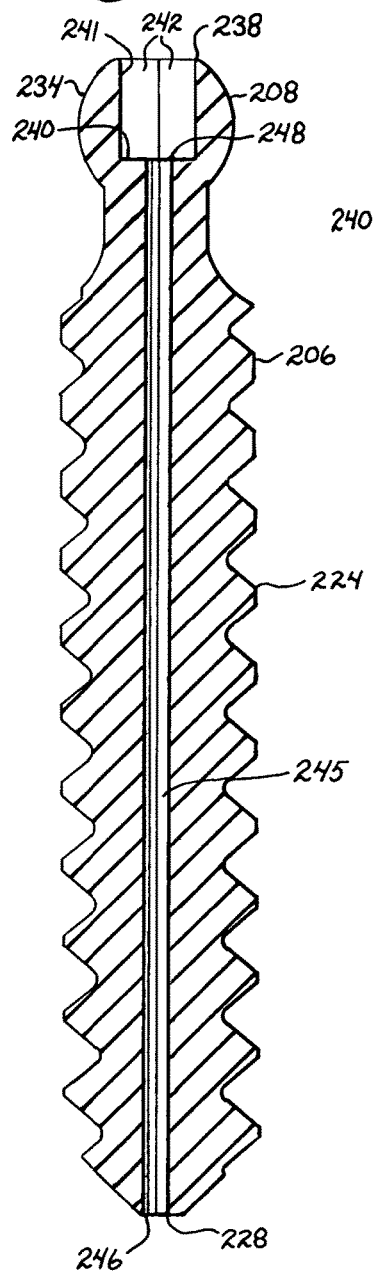
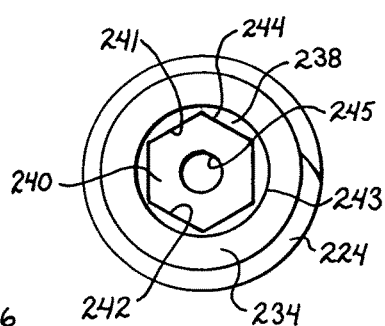

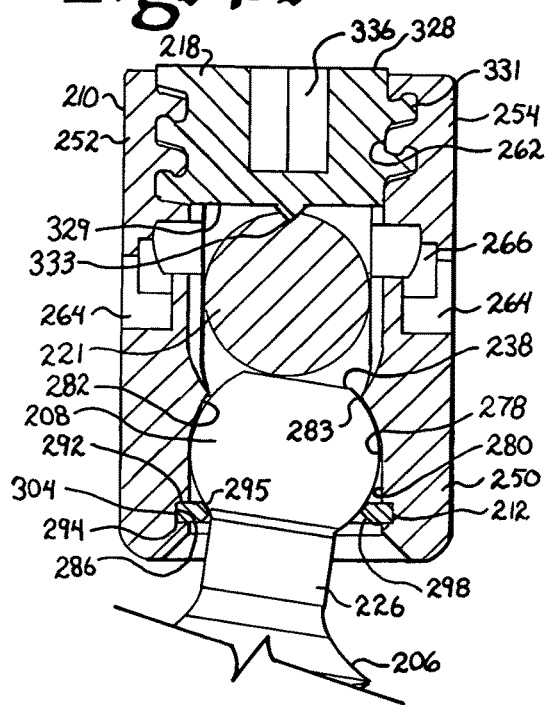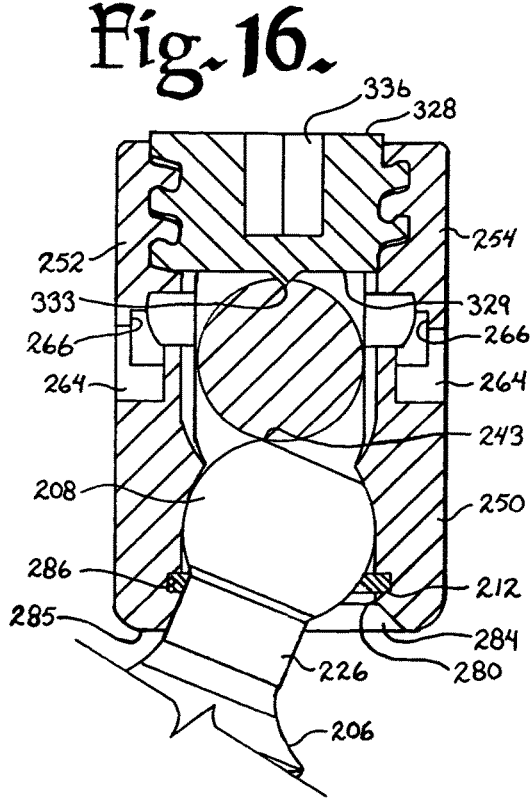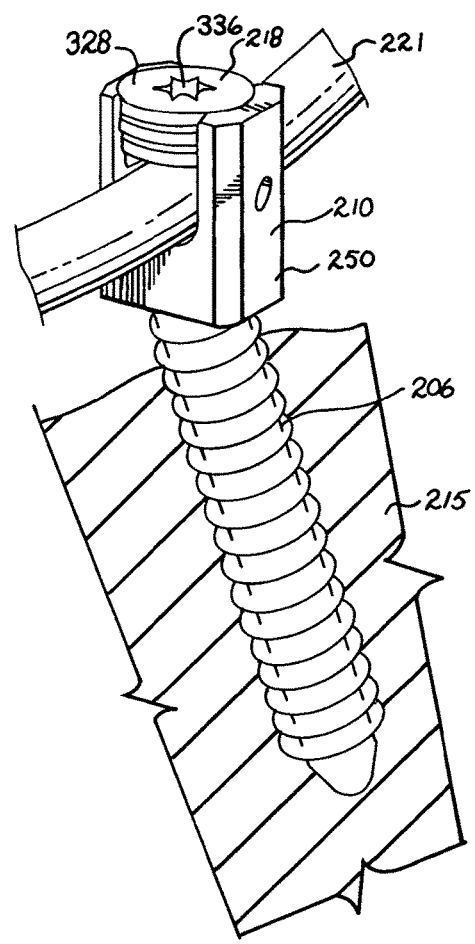

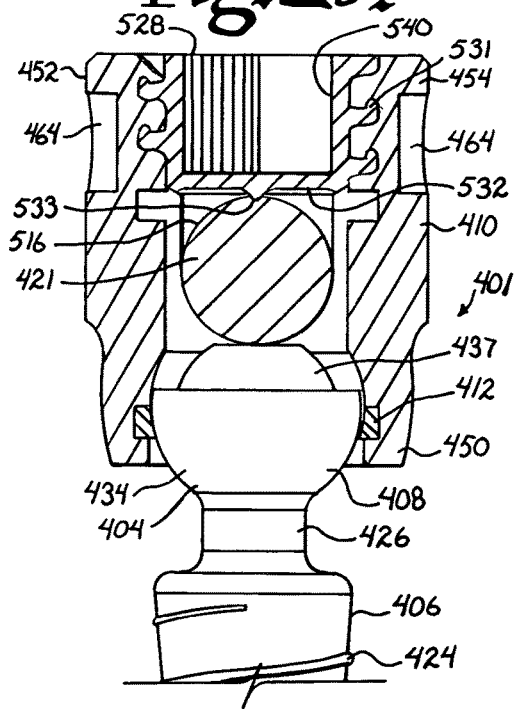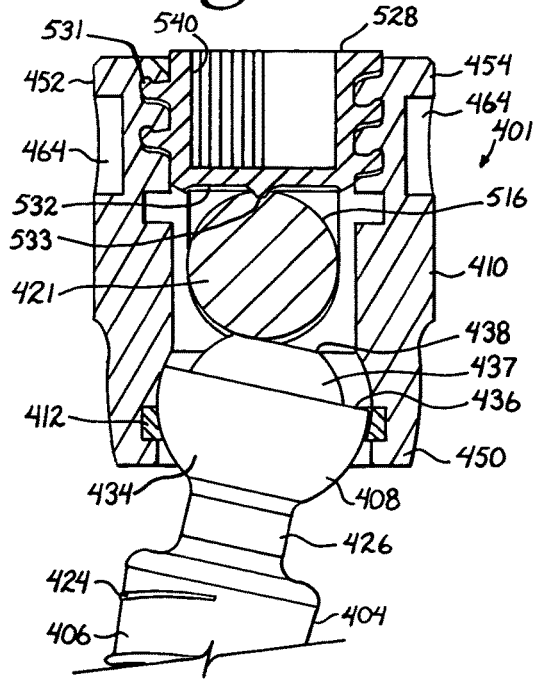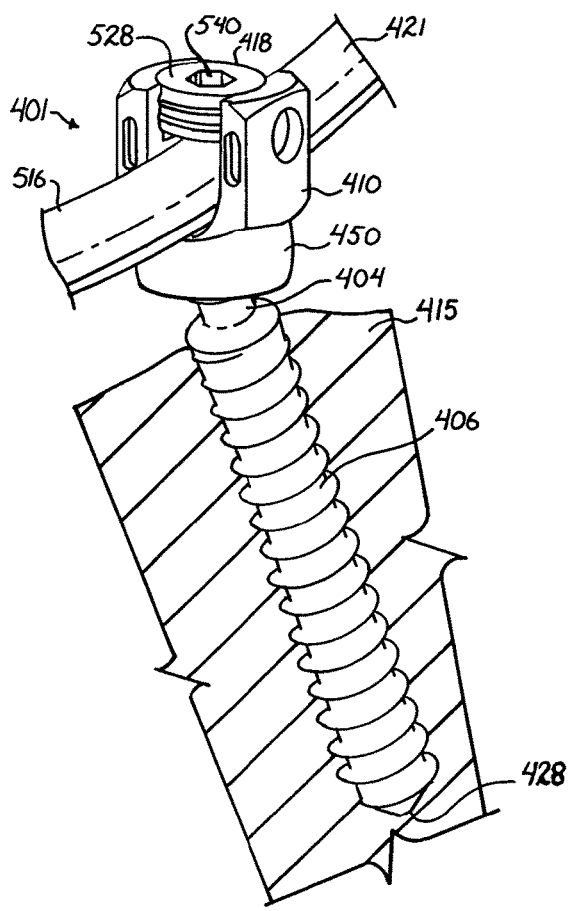

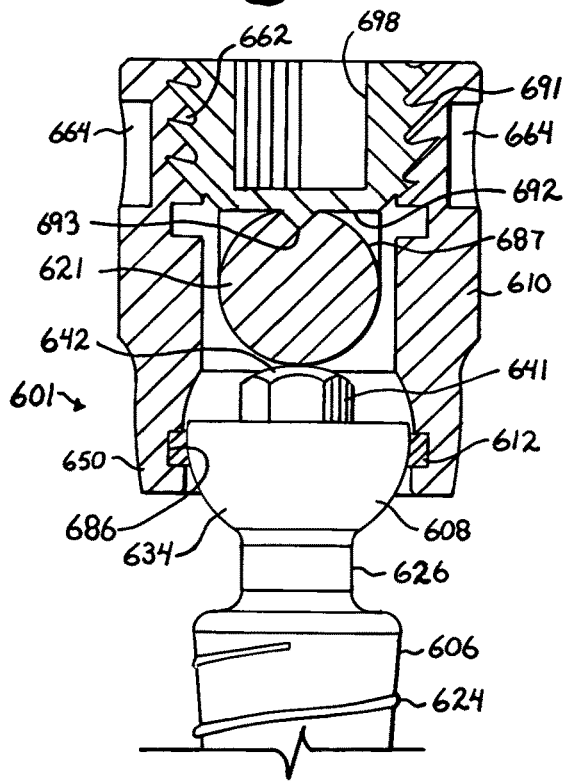
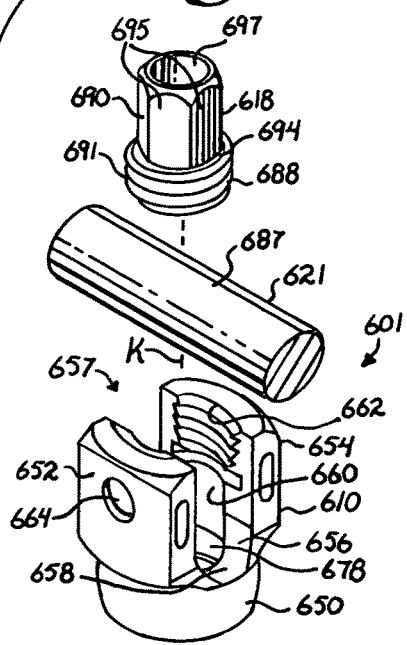
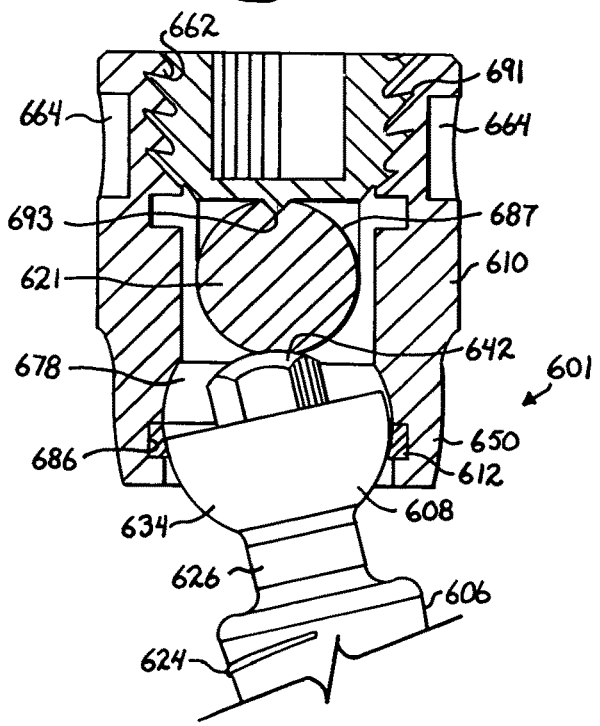
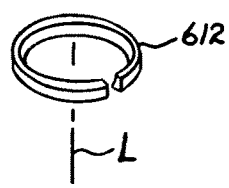

POLYAXIAL BONE SCREW ASSEMBLY WITH PARTIALLY SPHERICAL SCREW HEAD AND TWIST IN PLACE PRESSURE INSERT

CROSS REFERENCE TO RELATED APPLICATIONS

This application is a continuation-in-part of U.S. patent application Ser. No. 11/474,577, filed Jun. 26, 2006, now U.S. Pat. No. 8,366,7853, which claimed the benefit of U.S. Provisional Application No. 60/699,092 filed Jul. 14, 2005.

BACKGROUND OF THE INVENTION

The present invention is directed to polyaxial bone screws for use in bone surgery, particularly spinal surgery. Such screws have a rod receiver that can swivel about a shank of the bone screw, allowing the receiver to be positioned in any of a number of angular configurations relative to the shank.

Many spinal surgery procedures require securing various implants to bone and especially to vertebrae along the spine. For example, elongate rods are often utilized that extend along the spine to provide support to vertebrae that have been damaged or weakened due to injury or disease. Such rods must be supported by certain vertebrae and support other vertebrae.

The most common mechanism for providing vertebral support is to implant bone screws into certain bones which then in turn support the rod or are supported by the rod. Bone screws of this type may have a fixed head or receiver relative to a shank thereof. In the fixed bone screws, the receiver cannot be moved relative to the shank and the rod must be favorably positioned in order for it to be placed within the receiver. This is sometimes very difficult or impossible to do. Therefore, polyaxial bone screws are commonly preferred.

Polyaxial bone screws allow rotation of the receiver about the shank until a desired rotational position of the receiver is achieved relative to the shank. Thereafter, a rod can be inserted into the receiver and eventually the receiver is locked or fixed in a particular position relative to the shank.

A variety of polyaxial or swivel-head bone screw assemblies are available. One type of bone screw assembly includes an open receiver that allows for placement of a rod within the receiver. A closure top or plug is then used to capture the rod in the receiver of the screw.

Because such implants are for placement within the human body, it is desirable for the implant to have as little effect on the body as possible. Consequently, heavy, bulky implants are undesirable and lighter implants with a relatively small profile both in height and width are more desirable. However, a drawback to smaller, lighter implants is that they may be more difficult to rigidly fix to each other and into a desired angular position. Lack of bulk may also mean lack of strength, resulting in slippage under high loading. Also, more component parts may be required to rigidly fix the implant in a desired position. A further drawback of smaller components is that they may be difficult to handle during surgery because of their small size or fail to provide adequate driving or gripping surfaces for tools used to drive the shank into bone or drive the closure top into the screw head.

SUMMARY OF THE INVENTION

A polyaxial bone screw assembly of the present invention includes a shank having a body for fixation to a bone and an upper portion receivable in a cavity of a receiver. A retaining structure, preferably a collar-like retaining ring is also receivable in the cavity. The retaining structure is resilient and open, including first and second spaced ends being movable toward and away from one another. The shank upper portion and the retaining structure are sized and shaped to be bottom loadable into the receiver, with the retaining structure being compressed during insertion. Upon expanding to an original form, the retaining structure engages the receiver and captures the shank upper portion within a cavity of the receiver.

Another aspect of the invention is a tool engagement formation on or in the shank upper portion, allowing for non-slip engagement by a tool for driving the bone screw shank into bone. The tool engagement formation may be in the form of an axial projection or an internal drive having one or more apertures. The illustrated receiver includes an open channel communicating with the cavity that receives the shank upper portion and the retaining structure. The channel is sized and shaped for receiving a rod or other structural member and includes arms with a discontinuous guide and advancement structure for mating with a guide and advancement structure of a closure structure. The guide and advancement structure is preferably a flange form or other splay resistant guide and advancement structure. The shank upper portion is sized, shaped and positioned to receive a downward force with a rod seated in the channel. In operation, a closure structure operably applies a force through a rod that is transmitted onto the upper portion of the bone screw shank, which in turn frictionally engages both a spherical surface of the retaining structure and a spherical surface of the cavity thereby fixing the bone screw shank body in a selected angular orientation with respect to the receiver.

OBJECTS AND ADVANTAGES OF THE INVENTION

Therefore, objects of the present invention include providing a polyaxial bone screw assembly with features that may be readily, securely fastened to each other and to bone. Furthermore, it is an object of the invention to provide a lightweight, low profile polyaxial bone screw assembly that may be assembled prior to implantation and also assembles in such a manner that the components cooperate to create an overall structure that prevents unintentional disassembly. Another object of the invention is to provide a polyaxial bone screw assembly with a reduced number of components; specifically, in some embodiments, a bone screw assembly that does not require spacers, compression transfer members or other inserts for placement between a rod and the bone screw shank portion captured within the receiver. A further object of the invention is to provide a polyaxial bone screw assembly that is relatively easy to use, inexpensive to produce and especially well adapted for the intended usage thereof.

Other objects and advantages of the invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

FIG. 1 is an exploded perspective view of a polyaxial bone screw assembly according to the present invention having a shank, a receiver, and a retaining structure, and shown with a rod and a closure structure.

FIG. 2 is an enlarged top plan view of the retaining structure of FIG. 1.

FIG. 3 is a cross-sectional view taken along the line 3-3 of FIG. 2.

FIG. 4 is an enlarged cross-sectional view of the receiver, taken along the line 4-4 of FIG. 1.

FIG. 5 is an enlarged front elevational view of the shank of FIG. 1.

FIG. 6 is a cross-sectional view taken along the line 6-6 of FIG. 5.

FIG. 7 is an enlarged top plan view of the shank of FIG. 5.

FIG. 8 is an enlarged partial front elevational view of the shank of FIG. 1 shown fully assembled with the retaining structure, receiver, rod and closure structure of FIG. 1, with portions broken away to show the detail thereof.

FIG. 9 is a partial front elevational view with portions broken away similar to FIG. 8, showing an articulation of the shank with respect to the receiver.

FIG. 10 is a partial perspective view, showing the shank, receiver, retaining structure, rod and closure structure of FIG. 1 fully assembled and implanted in a vertebra, shown in cross-section.

FIG. 12 is an enlarged front elevational view of the shank of FIG. 11.

FIG. 13 is a cross-sectional view taken along the line 13-13 of FIG. 12.

FIG. 14 is an enlarged top plan view of the shank of FIG. 12.

FIG. 15 is an enlarged partial front elevational view of the shank of FIG. 11 shown fully assembled with the retaining structure, receiver, rod and closure structure of FIG. 11, with portions broken away to show the detail thereof.

FIG. 16 is a partial front elevational view with portions broken away similar to FIG. 15, showing an articulation of the shank with respect to the receiver.

FIG. 17 is a partial perspective view, showing the shank, receiver, retaining structure, rod and closure structure of FIG. 11 fully assembled and implanted in a vertebra, shown in cross-section.

FIG. 25 is an enlarged partial front elevational view of the shank of FIG. 18 shown fully assembled with the retaining structure, receiver, rod and closure structure of FIG. 18, with portions broken away to show the detail thereof.

FIG. 26 is a partial front elevational view with portions broken away similar to FIG. 25, showing an articulation of the shank with respect to the receiver.

FIG. 27 is a partial perspective view, showing the shank, receiver, retaining structure, rod and closure structure of FIG. 18 fully assembled and implanted in a vertebra, shown in cross-section.

FIG. 28 is an exploded perspective view of a fourth embodiment of a polyaxial bone screw assembly according to the present invention having a shank, a receiver, and a retaining structure, and shown with a rod and a closure structure.

FIG. 32 is an enlarged partial front elevational view of the shank of FIG. 28 shown fully assembled with the retaining structure, receiver, rod and closure structure of FIG. 28, with portions broken away to show the detail thereof.

FIG. 33 is a partial front elevational view with portions broken away similar to FIG. 32, showing an articulation of the shank with respect to the receiver.

DETAILED DESCRIPTION OF THE INVENTION

Figure 11:
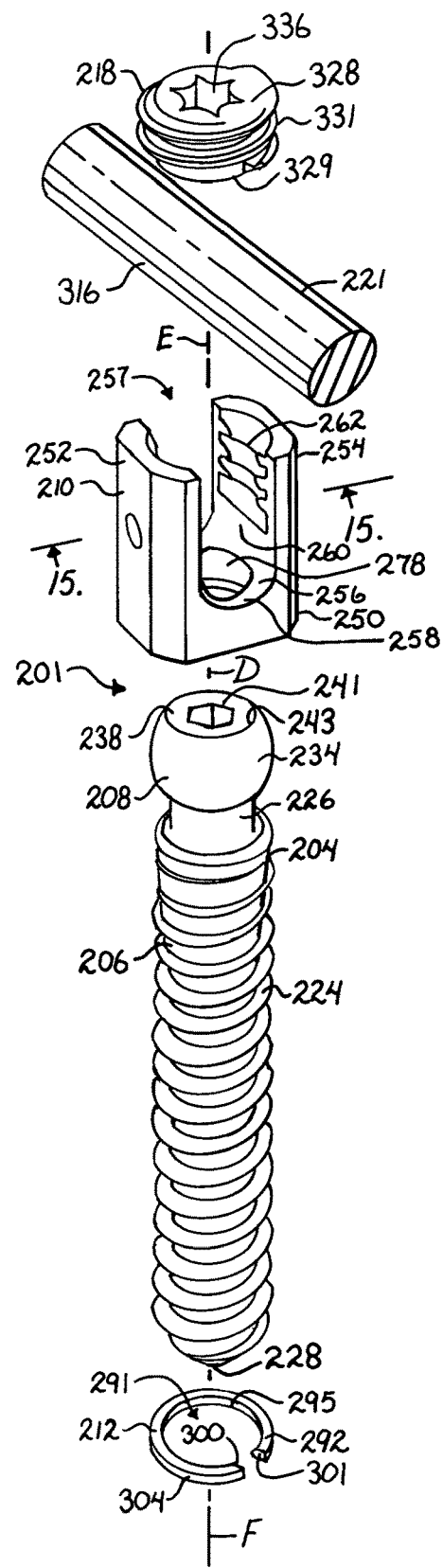
FIG. 11 is an exploded perspective view of a second embodiment of a polyaxial bone screw assembly according to the present invention having a shank, a receiver, and a retaining structure, and shown with a rod and a closure structure.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

With reference to FIGS. 1-10, the reference numeral 1 generally represents a polyaxial bone screw assembly according to the present invention. The assembly 1 includes a shank 4 that further includes a body 6 integral with an upwardly extending upper portion or capture structure 8; a receiver 10; and an independent open retaining structure 12. The shank 4, the receiver 10 and the retaining structure 12 preferably are assembled prior to implantation of the shank body 6 into a vertebra 15.

FIGS. 1 and 8-10 further show a closure structure 18 for compressing and biasing a longitudinal member such as a rod 21 against the shank upper portion 8 biasing the upper portion 8 into fixed frictional contact with the retaining structure 12 installed in the receiver 10, so as to fix the rod 21 relative to the vertebra 15. The receiver 10, the retaining structure 12 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near an end of an implantation procedure.

The shank 4, best illustrated in FIGS. 1 and 5-7, is elongate, with the shank body 6 having a helically wound bone implantable thread 24 extending from near a neck 26 located adjacent to the capture structure 8 to a tip 28 of the body 6 and extending radially outwardly therefrom. During use, the body 6 utilizing the thread 24 for gripping and advancement is implanted into the vertebra 15 leading with the tip 28 and driven down into the vertebra 15 with an installation or driving tool (not shown), so as to be implanted in the vertebra 15 to near the neck 26, as shown in FIG. 10, and as is described more fully in the paragraphs below. The shank 4 has an elongate axis of rotation generally identified by the reference letter A. It is noted that any reference to the words top, bottom, up and down, and the like, in this application refers to the alignment shown in the various drawings, as well as the normal connotations applied to such devices, and is not intended to restrict positioning of the assembly 1 in actual use.

The neck 26 extends axially outwardly and upwardly from the shank body 6. With particular reference to FIGS. 5 and 6, the illustrated neck 26 is of reduced radius as compared to the shank body 6 and an outer diameter of the thread 24. Further extending axially and outwardly from the neck 26 is the shank upper portion 8 that provides a connective or capture structure disposed at a distance from the thread 24 and thus at a distance from the vertebra 15 when the body 6 is implanted in the vertebra 15.

The shank upper portion 8 is configured for connecting the shank 4 to the receiver 10 and capturing the shank 4 in the receiver 10. With particular reference to FIGS. 1 and 5-7, the upper portion 8 has an outer, convex and partially spherical or hemispherical surface 34 that extends outwardly and upwardly from the neck 26 and terminates at a substantially annular surface 38. The spherical surface 34 has an outer radius configured for sliding cooperation and ultimate frictional mating with both a concave surface of the retaining structure 12 and a partially spherical inner surface of the receiver 10, having a substantially similar radius, discussed more fully in the paragraphs below. This configuration and arrangement provides for greater surface contact and better frictional engagement between the components compared to the prior art. The flat surface 38 is substantially perpendicular to the axis A. The spherical surface 34 shown in the present embodiment is smooth, but it is foreseen that such surface may include a roughened or textured surface or surface finish, or may be scored, knurled, or the like, for enhancing frictional engagement with the retaining structure 12 and the receiver 10. A counter sunk substantially planar base or seating surface 40 also is disposed perpendicular to the axis A and extends radially from a centrally located tool engagement structure 41. The sunken seating surface 40 is disposed between the tool engagement structure and the surface 38. The structure 41 has a top 42 and six driving faces 43 that form a hexagonal extension head driving structure mateable with a socket driving tool (not shown). The base 40 also includes a hexagonal outer perimeter 44 defined by outer driving faces that are parallel to the axis A and terminate at the surface 38. The tool engagement structure 41 is coaxial with the bone screw body 6 and extends along the axis A. In operation, a driving tool (not shown) fits about and engages the tool engagement structure 41 at the faces 43 for both driving and rotating the shank body 6 into the vertebra 15. A bottom of the driving tool may abut against the base 40 and also the faces defining the outer hexagonal perimeter 44, providing additional surfaces for engagement with the driving tool. It is foreseen that in other embodiments according to the invention, the driving features of the bone screw shank may take a variety of forms, including internal and external drives of different shapes and sized. As will be described with respect to the bone screw assembly 601 below, in smaller embodiments, a curved, concave surface may extend from the tool engagement structure to the outer spherical surface, allowing for the tool engagement structure to be designed with a somewhat longer axial length and thus providing a greater surface area for engagement with a driving tool, but without the planar seating surface 40 and additional planar driving faces because of the limitation of the small size of such a bone screw.

The top end surface 42 of the shank 4 is preferably curved or dome-shaped as shown in the drawings, for simple smooth contact engagement or positive mating engagement with the rod 21, when the bone screw assembly 1 is assembled, as shown in FIGS. 8 and 9 and in any angular arrangement of the shank 4 relative to the receiver 10. In the illustrated embodiment the surface 42 is smooth. While not required in accordance with the practice of the invention, the surface 42 may be scored, knurled or the like to further increase frictional positive mating engagement between the surface 42 and the rod 21.

The shank 4 shown in the drawings is cannulated, having a small central bore 45 extending an entire length of the shank 4 along the axis A, coaxial with the threaded body 6. The bore 45 has a first circular opening 46 at the shank tip 28 and a second circular opening 48 at the top surface 42. The bore 45 provides a passage through the shank 4 interior for a length of wire (not shown) inserted into the vertebra 15 prior to the insertion of the shank body 6, the wire providing a guide for insertion of the shank body 6 into the vertebra 15.

Referring to FIGS. 1 and 4, the receiver 10 has a generally U-shaped appearance with a discontinuous partially cylindrical inner profile and a faceted outer profile. The receiver 10 includes a base 50 integral with a pair of upstanding arms 52 and 54 forming a U-shaped cradle and defining a U-shaped channel 56 between the arms 52 and 54 with an upper opening 57 and a lower seat 58 having substantially the same radius as the rod 21 for operably snugly receiving the rod 21.

Each of the arms 52 and 54 has an interior surface 60 that in part defines the inner cylindrical profile and includes a partial helically wound guide and advancement structure 62 having an axis of rotation B. In the illustrated embodiment, the guide and advancement structure 62 is a partial helically wound interlocking flangeform configured to mate under rotation with a similar structure on the closure structure 18, as described more fully below. However, it is foreseen that the guide and advancement structure 62 could alternatively be another type of splay preventing structure such as a buttress thread, a square thread, a reverse angle thread or other thread like or non-thread like helically wound discontinuous advancement structure for operably guiding under rotation and advancing the closure structure 18 downward between the arms 52 and 54, as well as eventual torquing when the closure structure 18 abuts against the rod 21.

Tool engaging apertures or grip bores 64 are formed within the arms 52 and 54 and may be used for holding the receiver 10 during assembly with the shank 4 and the retaining structure 12 and also during the implantation of the shank body 6 into a vertebra 15. A holding tool (not shown) and the apertures 64 can be configured for a snap on/spring off, snap on/twist off, twist on/twist off, twist on/pry off or other flexible engagement wherein the holding tool has flexible legs which splay outwardly to position the tool for engagement in the apertures 64. It is noted that the apertures 64 the cooperating holding tool may be configured to be of a variety of sizes and locations along any of the surfaces of the arms 52 and 54. In the illustrated embodiment, the apertures 64 communicate with upwardly projecting hidden recesses 66 to further aid in securely holding the receiver 10 to a holding tool.

Communicating with and located beneath the U-shaped channel 56 of the receiver 10 is a chamber or cavity 78 substantially defined by an inner, substantially spherical or partially cylindrical surface 80 of the base 50 and an inner substantially spherical concave surface 82 that communicates with the U-shaped channel 56. The spherical surface 82 is disposed between the channel 56 and the inner surface 80. A circumferential ridge 83 is formed at the intersection of the inner surface 60 and the inner substantially spherical surface 82. The substantially spherical surface 82 is sized and shaped for slidable mating and eventual frictional engagement with the shank upper portion 8, having a radius that is approximately the same as a radius of the convex surface 34 of the shank upper portion 8 as described more fully below. The concave spherical surface 82 opens or widens at the lower surface 80, the surface 80 being sized to receive a shank upper portion 8 bottom loaded at a lower opening 84 of the receiver 10 where the surface 80 opens to an exterior 85 of the base 50. It is foreseen that if desired, some of the lower surface 80 may be cylindrical in nature (similar to the surface 280 of the assembly 201), rather than partially spherical as shown in FIG. 4. The spherical surface 82 provides a stop, upper shoulder or barrier near and at the ridge 83 prohibiting the shank upper portion 8 from being removable through the channel 56. The lower inner surface that opens to the exterior 85 of the base 50 is coaxially aligned with respect to the rotational axis B of the receiver 10 and is sized and shaped to receive the shank upper portion 8 therethrough and also receive the retaining structure 12 when the structure 12 is in a compressed configuration as will be described in greater detail below. Formed in a portion of the surface 80 near the spherical inner surface 82 is a circumferential recess or groove 86 that is sized and shaped to receive the retaining structure 12 when the structure 12 is in an uncompressed position as will also be discussed further below, so as to form a restriction at the location of the groove 86 to prevent the uncompressed retaining structure 12 from passing from the cavity 78 and out the lower opening 84 of the receiver 10 when the retaining structure 12 is loaded and seated in the groove 86, thereby also retaining the shank upper portion 8 within the cavity 78. Between the groove 86 and the opening 84 communicating with the base exterior 85, the receiver includes a chamfer or conical surface 88. As illustrated in FIG. 9, the surface 88 provides additional clearance for an angled or articulated bone screw shank 4 with respect to the receiver 10.

The retaining structure or collar 12 that is used to retain the capture structure 8 of the shank 4 within the receiver 10 is best illustrated by FIGS. 1-3. The structure 12 has a central axis C that is operationally the same as the axis B associated with the receiver 10 when the capture structure 8 and the retaining structure 12 are installed within the receiver 10. The retaining structure 12 has a central channel or hollow 91 that passes entirely through the structure 12 from a top surface 92 to a bottom surface 94 thereof. Surfaces that define the channel 91 include a discontinuous inner spherical surface 95 adjacent the top surface 92; an edge 97 adjacent the surface 95 and coaxial with the axis C; and a discontinuous conical surface, bevel or chamfer 98 sloping away from the axis C, adjacent the edge 97 and terminating at the bottom surface 94. The spherical surface 95 has a radius sized and shaped to cooperate with a radius of the substantially spherical surface 34 of the shank upper portion 8 such that the surface 95 slidingly and pivotally mates with the spherical surface 34 as described more fully below. The surface 95 may include a roughening or surface finish for providing additional frictional contact between the surface 95 and the surface 34, once a desired angle of articulation of the shank 4 with respect to the receiver 10 is reached.

The resilient retaining structure 12 includes first and second end surfaces, 100 and 101 disposed in spaced relation to one another and an outer substantially cylindrical surface 104. Both end surfaces 100 and 101 are disposed substantially perpendicular to the top surface 92 and the bottom surface 94. A width X between the surfaces 100 and 101 is determined by a desired amount of compressibility of the open retaining structure 12 when loaded into the receiver 10. The space X shown in FIG. 2 provides adequate space between the surfaces 100 and 101 for the retaining structure 12 to be pinched, with the surfaces 100 and 101 compressed toward one another to an almost touching or touching configuration, to an extent that the compressed retaining structure 12 is up or bottom loadable through the opening 84. After passing through the opening 84 and along a portion of the lower inner surface, the retaining structure 12 expands or springs back to an original uncompressed, rounded or collar-like configuration of FIG. 2 once in the groove 86. The embodiment shown in FIG. 2 illustrates the surfaces 100 and 101 as substantially parallel and vertical, however, it is foreseen that it may be desirable to orient the surfaces obliquely or at a slight angle depending upon the amount of compression desired during loading of the retaining and articulating structure 12 into the receiver 10.

FIGS. 8 and 9 illustrate the structure 12 installed in the groove 86 of the receiver 10 and in engagement with the shank upper portion 8. FIG. 8 illustrates the shank 4, receiver 10 and retaining structure 12 in co-axial alignment. In other words, axes A, B and C are aligned. FIG. 9 illustrates an articulating or swiveling relationship between the upper portion 8 and the installed retaining structure 12 wherein the bone screw upper portion 8 is slidable with respect to the retaining structure 12 at the surface 95, resulting in an orientation wherein the axis A of the shank 4 is not axially aligned with, but rather disposed at an angle with respect to the axes B and C of the receiver 10 and the retaining structure 12 respectively.

The elongate rod or longitudinal member 21 that is utilized with the assembly 1 can be any of a variety of implants utilized in reconstructive spinal surgery, but is normally a cylindrical elongate structure having a smooth cylindrical surface 116 of uniform diameter. The rod 21 is preferably sized and shaped to snugly seat near the bottom of the U-shaped channel 56 of the receiver 10 and, during normal operation, is positioned slightly above the bottom of the channel 56 at the lower seat 58. In particular, the rod 21 normally directly or abuttingly engages the shank top surface 42, as shown in FIGS. 8 and 9 and is biased against the domed shank top surface 42, consequently biasing the shank 4 downwardly in a direction toward the base 50 of the receiver 10 when the assembly 1 is fully assembled. For this to occur, the shank top surface 42 must extend at least slightly into the space of the channel 56 when engaging the retaining structure 12. The shank 4 is thereby locked or held in position relative to the receiver 10 by the rod 21 firmly pushing downward on the shank top surface 42.

With reference to FIGS. 1 and 8-10, the closure structure or closure top 18 can be any of a variety of different types of closure structures for use in conjunction with the present invention with suitable mating structure on the upstanding arms 52 and 54. In the embodiment shown, the closure top 18 is rotatably received between the spaced arms 52 and 54. It is foreseen that a mating and advancement structure could be located on the external surfaces of the arms 52 and 54 for mating with a closure top.

The illustrated closure top 18 has a generally cylindrical shaped base 128 with an upwardly extending break-off head 130. The base 128 includes a helically wound guide and advancement structure 131 that is sized, shaped and positioned so as to engage the guide and advancement structure 62 on the arms 52 and 54 to provide for rotating advancement of the closure structure 18 into the receiver 10 when rotated clockwise and, in particular, to cover the top or upwardly open portion 57 of the U-shaped channel 56 to capture the rod 21, preferably without splaying of the arms 52 and 54. The base 128 has a lower or bottom surface 132 with a centrally located pointed projection 133 for engaging and penetrating the rod 21 at the rod surface 116. In certain embodiments according to the invention, a circumferential rim (not shown) may also extend from the bottom surface 132, the rim providing additional engagement points with the rod surface 116. The closure structure 18 operably biases against the rod 21 by advancement and applies pressure to the rod 21 under torquing, so that the rod 21 is urged downwardly against the shank top end surface 42 that extends into the channel 56. Downward biasing of the shank top surface 42 operably produces a frictional engagement between the rod 21 and the surface 42 and also urges the shank upper portion 8 toward the retaining structure 12 that has been loaded into the receiver 10 and expanded into the groove 86, so as to frictionally engage the spherical surface 34 of the shank upper portion 8 with the spherical surface 95 of the retaining structure 12 fixing the shank 4 in a selected, rigid position relative to the receiver 10.

The closure structure break-off head 130 is secured to the base 128 at a neck 134 that is sized and shaped so as to break away at a preselected torque that is designed to properly seat the shank upper portion 8 in the receiver 10. The break-off head 130 includes an external faceted surface 135 that is sized and shaped to receive a conventional mating socket type head of a driving tool (not shown) to rotate and torque the closure structure 18. The break-off head 130 also includes a central bore 137 and one or more grooves 138 for operably receiving manipulating tools. Alternatively, a closure structure for use with the assembly 1 may not include a break-off head, but rather simply have a cylindrical body with a guide and advancement structure thereon and a top surface with an internal tool engagement structure formed therein, such as a hex aperture or a variety of internal tool-engaging forms of various shapes, such as a multi-lobular aperture sold under the trademark TORX, or the like.

The illustrated closure structure 18 also includes an internal drive removal tool engagement structure 140 in the form of an axially aligned aperture having a hex shape, disposed in the base 128. The internal drive or aperture 140 is accessible after the break-off head 130 breaks away from the base 128. The drive 140 is designed to receive a hex tool, of an Allen wrench type, for rotating the closure structure base 128 subsequent to installation so as to provide for removal thereof, if necessary. Such a tool engagement structure may take a variety of tool-engaging forms and may include one or more apertures of various shapes, such as a pair of spaced apart apertures, or a left hand threaded bore, or an easyout engageable step down bore, or a multi-lobular aperture, such as those sold under the trademark TORX, or the like.

Prior to the polyaxial bone screw assembly 1 being placed in use according to the invention, the retaining structure 12 is preferably first inserted about the bone screw shaft 6 until it is positioned around the shaft neck 26. This may be accomplished by either placing the structure 12 over the tip 28 and moving the structure 12 toward the upper portion 8 with the shaft 6 extending through the central channel 91 or inserting the structure 12 on the bone screw 4 at the neck 26 of the shank body 6, with the end surfaces 100 and 101 being pulled away from one another and pressed against and about the neck 26 until the surfaces 100 and 101 expand around the neck 26 and then spring back into a first position with the inner surface 95 facing the surface 34 of the shank upper portion 8. The shank upper portion 8 and the connected structure 12 are then simultaneously up or bottom-loaded into the receiver through the opening 84 with the upper portion 8 being placed into the cavity 78. The structure 12 is manually compressed by pinching the surfaces 100 and 101 toward one another as the neck 26 is placed into the opening 84 until the structure 12 is aligned with the groove 86. The compressive force is then removed and the structure 12 resiliently springs back and returns to the original ring-like or collar-like orientation. Then, as illustrated in FIGS. 8 and 9, the top surface 92, bottom surface 94 and outer cylindrical surface 104 of the structure 12 frictionally engage the groove 86, fixing the retaining structure 12 in the receiver 10 and capturing the shank upper portion 8 within the receiver and in sliding, pivotal relationship with the spherical surface 95 of the retaining structure 12, and in certain angular orientations or articulations, with the spherical surface 82 of the receiver 10.

In an alternative method of installation, the bone screw shank upper portion 8 is first placed in the receiver 10 by inserting the upper portion 8 through the opening 84 and into the cavity 78. The retaining structure 12 may then be placed over the shank body 6 at the tip 28 and moved toward the shank upper portion 8. As with the previously described installation method, the structure 12 is manually compressed by pinching the surfaces 100 and 101 toward one another as the structure 12 is placed in the opening 84 until the structure 12 is aligned with the groove 86. The compressive force is then removed and the structure 12 resiliently springs back and returns to the original ring-like or collar-like orientation, fixing the structure 12 in the receiver 10 and capturing the shank upper portion 8 within the receiver cavity 78.

The capture structure 8 may then be manipulated into a position substantially coaxial with the receiver 10 in readiness for bone implantation. The assembly 1 is typically screwed into a bone, such as the vertebra 15, by rotation of the shank 4 using a driving tool (not shown) that operably drives and rotates the shank 4 by engagement thereof with the faces 43 of the hexagonally shaped tool engagement structure 41 of the shank 4. Preferably, when the driving tool engages the structure 41, a bottom or end portion thereof abuts the countersunk planar seating surface 40 and outer surfaces of the driving tool engage the walls that define the outer perimeter 44, providing an additional driving interface.

Typically, the receiver 10 and the retaining structure 12 are assembled on the shank 4 before inserting the shank body 6 into the vertebra 15 as previously described hereon. However, it is foreseen that in certain circumstances, the shank body 6 can be first partially implanted with the capture structure 8 extending proud to allow placement of the retaining structure 12 about the neck 26, followed by assembly with the receiver 10. Then the shank body 6 can be further driven into the vertebra 15.

The vertebra 15 may be pre-drilled to minimize stressing the bone and have a guide wire (not shown) inserted to provide a guide for the placement and angle of the shank 4 with respect to the vertebra 15. A further tap hole may be made using a tap with the guide wire as a guide. Then, the assembly 1 or the solitary shank 4, is threaded onto the guide wire utilizing the cannulation bore 45 by first threading the wire into the bottom opening 46 and then out of the top opening 48. The shank 4 is then driven into the vertebra 15, using the wire as a placement guide.

With reference to FIGS. 8 and 9, the rod 21 is eventually positioned within the receiver U-shaped channel 56, and the closure structure or top 18 is then inserted into and advanced between the arms 52 and 54 so as to bias or push against the rod 21. The break-off head 130 of the closure structure 18 is twisted to a preselected torque, for example 90 to 120 inch pounds, to urge the rod 21 downwardly. The shank top end surface 42, because it is rounded to approximately equally extend upward into the channel 56 approximately the same amount no matter what degree of rotation exists between the shank 4 and receiver 10 and because the surface 42 is sized to extend upwardly into the U-shaped channel 56, the surface 42 is engaged by the rod 21 and pushed downwardly toward the base 50 of the receiver 10 when the closure structure 18 biases downwardly toward and onto the rod 21. The downward pressure on the shank 4 urges the shank top portion 8 downward toward the retaining structure 12 and possibly against the receiver seating surface 82. As the closure structure 18 presses against the rod 21, the rod 21 presses against the shank upper portion 8 that becomes frictionally, rigidly attached to the receiver 10 at its spherical surface 82 and at the retaining structure 12 spherical surface 95.

As previously described, FIG. 8 illustrates the polyaxial bone screw assembly 1 and including the rod 21 and the closure structure 18 positioned at a level or extent of articulation in which the axis A of the bone screw shank and the axis B of the receiver are coaxial. FIGS. 9 and 10 illustrate the assembly 1 with the axis A of the bone shank 4 at an angle with respect to the axis B of the receiver 10, and with the shank 4 being fixed in such angular locked configuration and implanted in the vertebra 15.

If removal of the assembly 1 and the associated rod 21 and the closure structure 18 is necessary, disassembly is accomplished by using a driving tool (not shown) mating with driving surfaces of the aperture 140 on the closure structure 18 to rotate the base 138 and reverse the advancement thereof in the receiver 10. Then, disassembly of the assembly 1 is accomplished in reverse order to the procedure described previously herein for assembly.

With reference to FIGS. 11-17, the reference numeral 201 generally represents a second or alternative embodiment of a bone screw assembly according to the present invention. The assembly 201 includes a shank 204 that further includes a body 206 integral with an upwardly extending upper portion or capture structure 208; a receiver 210; and an independent open retaining structure 212. The shank 204, the receiver 210 and the retaining structure 212 preferably are assembled prior to implantation of the shank body 206 into a vertebra 215.

FIGS. 11 and 15-17 further show a closure structure 218 for compressing and biasing a longitudinal member such as a rod 221 against the shank upper portion 208 biasing the upper portion 208 into fixed frictional contact with the retaining structure 212 installed in the receiver 210, so as to fix the rod 221 relative to the vertebra 215. The receiver 210, the retaining structure 212 and the shank 204 cooperate in such a manner that the receiver 210 and the shank 204 can be secured at any of a plurality of angles, articulations or rotational alignments relative to one another and within a selected range of angles both from side to side and from front to rear, to enable flexible or articulated engagement of the receiver 210 with the shank 204 until both are locked or fixed relative to each other near an end of an implantation procedure.

The shank 204, best illustrated in FIGS. 11-14, is elongate, with the shank body 206 having a helically wound bone implantable thread 224 extending from near a neck 226 located adjacent to the shank upper portion 208 to a tip 228 of the body 206 and extending radially outwardly therefrom. During use, the body 206 utilizing the thread 224 for gripping and advancement is implanted into the vertebra 215 leading with the tip 228 and driven down into the vertebra 215 with an installation or driving tool (not shown), so as to be implanted in the vertebra 215 to near the neck 226, as shown in FIG. 17, and as is described more fully in the paragraphs below. The shank 204 has an elongate axis of rotation generally identified by the reference letter D.

The neck 226 extends axially outwardly and upwardly from the shank body 206. With particular reference to FIG. 12-13, the illustrated neck 226 is of reduced radius as compared to the shank body 206 and an outer diameter of the thread 224. Further extending axially and outwardly from the neck 226 is the shank upper portion 208 that provides a connective or capture structure disposed at a distance from the thread 224 and thus at a distance from the vertebra 215 when the body 206 is implanted in the vertebra 215.

The shank upper portion 208 is configured for connecting the shank 204 to the receiver 210 and capturing the shank 204 in the receiver 210. With particular reference to FIGS. 12-14, the upper portion 208 has an outer, convex and substantially spherical surface 234 that extends outwardly and upwardly from the neck 226 and terminates at a substantially planar top surface 238. The spherical surface 234 has an outer radius configured for sliding cooperation and ultimate frictional mating with a concave surface of the retaining structure 212 and a substantially spherical inner surface of the receiver 210, having a substantially similar radius, discussed more fully in the paragraphs below. The flat surface 238 is substantially perpendicular to the axis D. The spherical surface 234 shown in the present embodiment is smooth, but it is foreseen that the surface 234 may include a roughened or textured surface or surface finish, or may be scored, knurled, or the like, for enhancing frictional engagement with the retaining structure 212 and the receiver 210.

A counter sunk substantially planar base or seating surface 240 partially defines an internal drive feature or imprint 241. The illustrated internal drive feature 241 is an aperture formed in the top 238 and has a hex shape designed to receive a hex tool of an Allen wrench type, into the aperture for rotating and driving the bone screw shank 204. It is foreseen that such an internal tool engagement structure may take a variety of tool-engaging forms and may include one or more apertures of various shapes, such as a pair of spaced apart apertures or a multi-lobular aperture, such as those sold under the trademark TORX, or the like. The seat or base 240 of the drive feature 241 is disposed perpendicular to the axis D with the drive feature 241 otherwise being coaxial with the axis D. Six driving faces or walls 242, each disposed parallel to the axis D also define the feature 241. The planar top surface 238 extends from a hexagonal outer perimeter 244 defined by the driving faces 242 and terminates at a circular edge 243. The circular edge 243 also defines a top or terminating upper edge of the spherical outer surface 234. In operation, a driving tool (not shown) is received in the internal drive feature 241, being seated at the base 240 and engaging the faces 242 for both driving and rotating the shank body 206 into the vertebra 215.

The shank 204 shown in the drawings is cannulated, having a small central bore 245 extending an entire length of the shank 204 along the axis D, coaxial with the threaded body 206. The bore 245 has a first circular opening 246 at the shank tip 228 and a second circular opening 248 at the driving feature seating surface 240. The bore 245 provides a passage through the shank 204 interior for a length of wire (not shown) inserted into the vertebra 215 prior to the insertion of the shank body 206, the wire providing a guide for insertion of the shank body 206 into the vertebra 215.

Referring to FIGS. 11 and 15-16, the receiver 210 has an axis of rotation E and is substantially similar to the receiver 10 previously described herein. Thus, the description of the receiver 10 is incorporated by reference with respect to the receiver 210. Specifically, the receiver 210 includes a receiver base 250, arms 252 and 254, a U-shaped channel 256 with an upper opening 257, a lower seat 258, an interior surface 260, guide and advancement structure 262, grip bores 264, recesses 266, a chamber or cavity 278, a lower inner surface 280, an inner spherical surface 282, a ridge 283, a lower opening 284, a base exterior 285 and a groove 286 the same or substantially similar to the respective base 50, arms 52 and 54, U-shaped channel 56 with upper opening 57, lower seat 58, interior surface 60, guide and advancement structure 62, grip bores 64, recesses 66, cavity 78, lower inner surface 80, inner spherical surface 82, ridge 83, lower-opening 84, base exterior 85 and groove 86 previously described herein with respect to the receiver 10 of the assembly 1. As discussed earlier with respect to the assembly 1, as compared to the receiver 10, the receiver 210 lower surface 280 is substantially cylindrical while the lower surface 80 is mostly spherical.

The retaining structure or collar 212 that is used to retain the capture structure 208 of the shank 204 within the receiver 210 is best illustrated in FIGS. 11 and 15-16. The structure 212 has a central axis F that is operationally the same as the axis E associated with the receiver 210 when the capture structure 208 and the retaining structure 212 are installed within the receiver 210. The retaining structure 212 is the same or substantially similar to the retaining structure 12 previously described herein and thus the description of the structure 12 is incorporated by reference herein with respect to the structure 212. Specifically, the structure 212 includes a central channel 291, a top 292, a bottom 294, a partially spherical inner surface 295, a conical surface or chamfer 298, end surfaces 300 and 301 and an outer cylindrical surface 304, the same or substantially similar to respective central channel 91, top 92, bottom 94, spherical inner surface 95, conical surface 98, end surfaces 100 and 101 and outer cylindrical surface 104 of the retaining structure 12.

A width or space between the surfaces 300 and 301 is determined by a desired amount of compressibility of the open retaining structure 212 when loaded into the receiver 210. The space shown in FIG. 11 between the surfaces 300 and 301 provides an adequate distance between the surfaces 300 and 301 for the retaining structure 212 to be pinched, with the surfaces 300 and 301 compressed toward one another to an almost touching or touching configuration, to an extent that the compressed retaining structure 212 is up or bottom loadable through the opening 284. As illustrated in FIG. 11, the surfaces 300 and 301 are substantially parallel and vertical, however, it is foreseen that it may be desirable to orient the surfaces obliquely or at a slight angle depending upon the amount of compression desired during loading of the retaining and articulating structure 212 into the receiver 210. After passing through the opening 284 and along a portion of the cylindrical inner surface 280, the retaining structure 212 expands or springs back to an original uncompressed, rounded or collar-like configuration once in the groove 286. FIGS. 15 and 16 illustrate the structure 212 in a fully installed position in the receiver 210 and having an articulating or swiveling relationship with the upper portion 208 of the bone screw shank 204 wherein the bone screw upper portion 208 is slidable with respect to the retaining structure 212 at the surface 295.

The elongate rod or longitudinal member 221 that is utilized with the assembly 201 can be any of a variety of implants utilized in reconstructive spinal surgery, but is normally a cylindrical elongate structure having a smooth cylindrical surface 316 of uniform diameter. The rod 221 is preferably sized and shaped to snugly seat near the bottom of the U-shaped channel 256 of the receiver 210 and, during normal operation, is positioned slightly above the bottom of the channel 256 at the lower seat 258. In particular, the rod 221 directly or abutingly engages the upper portion 208 of the shank 204 either at the top 238, the circular edge 243 or the spherical surface 234, as shown in FIGS. 15 and 16, and is biased against the upper portion 208, consequently biasing the shank 204 downwardly in a direction toward the base 250 of the receiver 210 when the assembly 201 is fully assembled. For this to occur, the shank upper portion 208 must extend at least slightly into the space of the channel 256 when engaging the retaining structure 212. The shank 204 is thereby locked or held in position relative to the receiver 210 by the rod 221 firmly pushing downward on the shank upper portion 208.

With reference to FIGS. 11 and 15-17, the closure structure or closure top 218 can be any of a variety of different types of closure structures for use in conjunction with the present invention with suitable mating structure on the upstanding arms 252 and 254. In the embodiment shown, the closure top 218 is rotatably received between the spaced arms 252 and 254. It is foreseen that a mating and advancement structure could be located on the external surfaces of the arms 252 and 254 for mating with a closure top.

The illustrated closure structure 218 is substantially cylindrical, having a top 328 and a bottom 329. The closure structure 218 further includes a helically wound guide and advancement structure 331 that is sized, shaped and positioned so as to engage the guide and advancement structure 262 on the arms 252 and 254 to provide for rotating advancement of the closure structure 218 into the receiver 210 when rotated clockwise and, in particular, to cover the top or upwardly open portion 257 of the U-shaped channel 256 to capture the rod 221, preferably without splaying of the arms 252 and 254. The closure structure bottom 329 includes a centrally located pointed projection 333 for engaging and penetrating the rod 221 at the rod surface 316. In certain embodiments according to the invention, a circumferential rim (not shown) may also extend from the bottom surface 329, the rim providing additional engagement points with the rod surface 316. The closure structure 218 operably biases against the rod 221 by advancement and applies pressure to the rod 221, so that the rod 221 is urged downwardly against the shank upper portion 208 that extends into the channel 256. Downward biasing of the shank upper portion 208 operably produces a frictional engagement between the rod 221 and the upper portion 208 and also urges the shank upper portion 208 toward the retaining structure 212 that has been loaded into the receiver 210 and expanded into the groove 286, so as to frictionally engage the spherical surface 234 of the shank upper portion 208 with the spherical surface 295 of the retaining structure 212 fixing the shank 204 in a selected, rigid position relative to the receiver 210. It is noted that because the illustrated shank upper portion 208 includes the flat surface 238, circular edge 243 and spherical surface 234 and the rod 221 may engage any of such surfaces, the rod 221 may be seated at a distance from the receiver lower seat 258 and the closure structure 218 may not be disposed flush to a top of the receiver 210 when fully engaged with the rod 221 biasing the rod 221 into locking engagement with the shank 204. Such placement of the closure structure 218 and the rod 221 does not hinder the closure structure 218 from seating in the receiver 210 and fixing the rod 221 in a locked position within the receiver 210.

Formed in the closure structure 218 top surface 328 is an internal drive feature 336 sized and shaped to receive a mating driving tool (not shown) to rotate and torque the closure structure 218 against the rod 221. The illustrated drive feature 336 is multi-lobular, but it is foreseen that the internal drive feature may be a hex aperture or a variety of internal tool-engaging forms of various shapes. The drive feature 336 may also be used to remove the closure structure 218 from the receiver 210 subsequent to installation, if desired or necessary.

Prior to the polyaxial bone screw assembly 201 being placed in use according to the invention, the retaining structure 212 is preferably first inserted about the bone screw shaft 206. This may be accomplished by either placing the structure 212 over the tip 228 and moving the structure 212 toward the upper portion 208 with the shaft 206 extending through the central channel 291 or inserting the structure 212 on the bone screw 204 at the neck 226 of the shank body 206, with the end surfaces 300 and 301 being pulled away from one another and pressed against and about the neck 226 until the surfaces 300 and 301 expand around the neck 226 and then spring back into a first position with the inner surface 295 facing the surface 234 of the shank upper portion 208. The shank upper portion 208 and the connected structure 212 are then simultaneously up or bottom-loaded into the receiver through the opening 284 with the upper portion 208 being placed into the cavity 278. The structure 212 is manually compressed by pinching the surfaces 300 and 301 toward one another as the neck 226 is placed into the opening 284 until the structure 212 is aligned with the groove 286. The compressive force is then removed and the structure 212 resiliently springs back and returns to the original ring-like or collar-like orientation. Then, as illustrated in FIG. 15, the top surface 292, bottom surface 294 and outer cylindrical surface 304 of the structure 212 frictionally engage the groove 286, fixing the retaining structure 212 in the receiver 210 and capturing the shank upper portion 208 within the receiver and in sliding, pivotal relationship with the spherical surface 295 of the retaining structure 212 and with the spherical surface 282 of the receiver 210.

In an alternative method of installation, the bone screw shank upper portion 208 is first placed in the receiver 210 by inserting the upper portion 208 through the opening 284 and into the cavity 278. The retaining structure 212 may then be placed over the shank body 206 at the tip 228 and moved toward the shank upper portion 208. As with the previously described installation method, the structure 212 is manually compressed by pinching the surfaces 300 and 301 toward one another as the structure 212 is placed in the opening 284 until the structure 212 is aligned with the groove 286. The compressive force is then removed and the structure 212 resiliently springs back and returns to the original ring-like or collar-like orientation, fixing the structure 212 in the receiver 210 and capturing the shank upper portion 208 within the receiver cavity 278.

The capture structure 208 may then be manipulated into a position substantially coaxial with the receiver 210 in readiness for bone implantation. The assembly 201 is typically screwed into a bone, such as the vertebra 215, by rotation of the shank 204 using a driving tool (not shown) that operably drives and rotates the shank 204 by engagement thereof with the base 240 and the faces 242 of the internal drive feature 241.

Typically, the receiver 210 and the retaining structure 212 are assembled on the shank 204 before inserting the shank body 206 into the vertebra 215 as previously described hereon. However, it is foreseen that in certain circumstances, the shank body 206 can be first partially implanted with the capture structure 208 extending proud to allow placement of the retaining structure 212 about the neck 226, followed by assembly with the receiver 210. Then the shank body 206 can be further driven into the vertebra 215.

The vertebra 215 may be pre-drilled to minimize stressing the bone and have a guide wire (not shown) inserted to provide a guide for the placement and angle of the shank 204 with respect to the vertebra 215. A further tap hole may be made using a tap with the guide wire as a guide. Then, the assembly 201 or the solitary shank 204, is threaded onto the guide wire utilizing the cannulation bore 245 by first threading the wire into the bottom opening 246, then out of the top opening 248 and then through and out of the driving feature 241. The shank 204 is then driven into the vertebra 215, using the wire as a placement guide.

With reference to FIGS. 15-17, the rod 221 is eventually positioned within the receiver U-shaped channel 256, and the closure structure or top 218 is then inserted into and advanced between the arms 252 and 254 so as to bias or push against the rod 221 and urge the rod 221 downwardly. Depending on a desired amount of articulation between the shank body 206 and the receiver 210, the rod 221 comes into contacted with the planar top surface 238 (shown in FIG. 15), the circular edge 243 (shown in FIG. 16) or the spherical surface 234 of the shank upper portion 208 and such surface is engaged by the rod 221 and pushed downwardly toward the base 250 of the receiver 210 when the closure structure 218 biases downwardly toward and onto the rod 221. The downward pressure on the shank 204 urges the shank top portion 208 downward toward the retaining structure 212 and typically against the receiver seating surface 282. As the closure structure 218 presses against the rod 221, the rod 221 presses against the shank upper portion 208 that becomes frictionally, rigidly attached to the receiver 210 at the retaining structure 212.

FIGS. 15-17 illustrates the polyaxial bone screw assembly 201 and including the rod 221 and the closure structure 218 positioned at various articulations or locked angular orientations in which the axis D of the bone screw shank and the axis E of the receiver are not coaxial. FIG. 17 also shows the shank 204 implanted in the vertebra 15. As previously described, full locking installation is obtainable when the rod 221 engages the rim 243 or the spherical surface 234, even though such engagement places the rod 221 higher in the channel 256 and therefore the closure structure 218 does not seat in a manner that is flush with the top surface of the receiver 210.

If removal of the assembly 201 and the associated rod 221 and the closure structure 218 is necessary, disassembly is accomplished by using a driving tool (not shown) mating with the internal drive 336 on the closure structure 218 to rotate the structure 218 and reverse the advancement thereof in the receiver 210. Then, disassembly of the assembly 201 is accomplished in reverse order to the procedure described previously herein for assembly.

With reference to FIGS. 18-27, the reference numeral 401 generally represents a third or alternative embodiment of a bone screw assembly according to the present invention. The assembly 401 includes a shank 404 that further includes a body 406 integral with an upwardly extending upper portion or capture structure 408; a receiver 410; and an independent open retaining structure 412. The shank 404, the receiver 410 and the retaining structure 412 preferably are assembled prior to implantation of the shank body 406 into a vertebra 415.

FIGS. 18 and 25-27 further show a closure structure 418 for compressing and biasing a longitudinal member such as a rod 421 against the shank upper portion 408 biasing the upper portion 408 into fixed frictional contact with the retaining structure 412 installed in the receiver 410, so as to fix the rod 421 relative to the vertebra 415. The receiver 410, the retaining structure 412 and the shank 404 cooperate in such a manner that the receiver 410 and the shank 404 can be secured at any of a plurality of angles, articulations or rotational alignments relative to one another and within a selected range of angles both from side to side and from front to rear, to enable flexible or articulated engagement of the receiver 410 with the shank 404 until both are locked or fixed relative to each other near an end of an implantation procedure.

The shank 404, best illustrated in FIGS. 18 and 22-24, is elongate, with the shank body 406 having a helically wound bone implantable thread 424 extending from near a neck 426 located adjacent to the shank upper portion 408 to a tip 428 of the body 406 and extending radially outwardly therefrom. During use, the body 406 utilizing the thread 424 for gripping and advancement is implanted into the vertebra 415 leading with the tip 428 and driven down into the vertebra 415 with an installation or driving tool (not shown), so as to be implanted in the vertebra 415 to near the neck 426, as shown in FIG. 27, and similar to what has been described previously with respect to the similar bone screw assemblies 1 and 201. The shank 404 has an elongate axis of rotation generally identified by the reference letter G.

Figure 22:
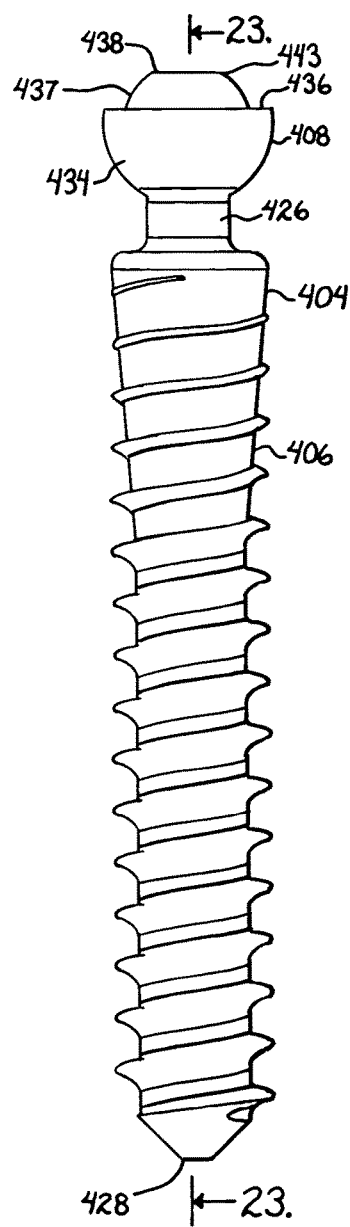
FIG. 22 is an enlarged front elevational view of the shank of FIG. 18.
Figure 23:
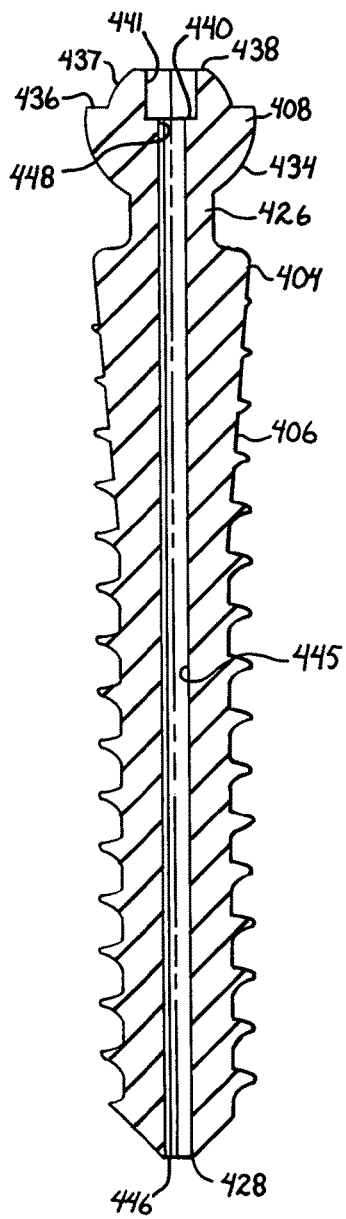
FIG. 23 is a cross-sectional view taken along the line 23-23 of FIG. 22.
Figure 24:
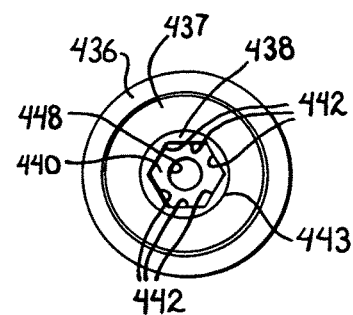
FIG. 24 is an enlarged top plan view of the shank of FIG. 22.

The neck 426 extends axially outwardly and upwardly from the shank body 406. With particular reference to FIGS. 22-23, the illustrated neck 426 is of reduced radius as compared to the shank body 406 and an outer diameter of the thread 424. Further extending axially and outwardly from the neck 426 is the shank upper portion 408 that provides a connective or capture structure disposed at a distance from the thread 424 and thus at a distance from the vertebra 415 when the body 406 is implanted in the vertebra 415.

The shank upper portion 408 is configured for connecting the shank 404 to the receiver 410 and capturing the shank 404 in the receiver 410. The upper portion 408 has an outer, lower, convex and partially spherical surface 434 that extends outwardly and upwardly from the neck 426 and terminates at a substantially planar annular surface 436. A second, upper convex partially spherical surface 437 extends from the planar surface 436 to a planar and annular top surface 438.

The lower spherical surface 434 is substantially hemispherical and has an outer radius configured for sliding cooperation and ultimate frictional mating with a concave surface of the retaining structure 412 and a substantially spherical inner surface of the receiver 410, having a substantially similar radius, discussed more fully below. The planar or flat surfaces 436 and 438 are both substantially perpendicular to the shank axis G. The partially spherical surface 434 shown in the present embodiment is smooth, but it is foreseen that the surface 434 may include a roughened or textured surface or surface finish, or may be scored, knurled, or the like, for enhancing frictional engagement with the retaining structure 412 and the receiver 410.

The upper, partially spherical surface 437 has a radius that is smaller than the radius of the lower spherical surface 434. A compared to the assembly 201 that has the shank 204 with the substantially spherical surface 234, the pair of spherical surfaces 434 and 437 of the shank upper portion 408 cooperate with the smaller upper spherical surface 437 providing a more compact structure with greater clearance between the upper spherical surface 437 and the inner walls of the receiver 410 than available to the single spherical surface 234, allowing for ease in articulation and a slightly greater degree of angulation of the shank 408 with respect to the receiver 410 than provided by the assembly 201.

A counter sunk substantially planar base or seating surface 440 partially defines an internal drive feature or imprint 441. The illustrated internal drive feature 441 is an aperture formed in the top 438 and has a hex shape designed to receive a hex tool of an Allen wrench type, into the aperture for rotating and driving the bone screw shank 404. It is foreseen that such an internal tool engagement structure may take a variety of tool-engaging forms and may include one or more apertures of various shapes, such as a pair of spaced apart apertures or a multi-lobular aperture, such as those sold under the trademark TORX, or the like. The seat or base 440 of the drive feature 441 is disposed perpendicular to the axis G with the drive feature 441 otherwise being coaxial with the axis G. Six driving faces or walls 442, each disposed parallel to the axis G also define the feature 441. The planar top surface 438 extends from a hexagonal outer perimeter 444 defined by the driving faces 442 and terminates at a circular edge 443. The circular edge 443 also defines a top or terminating upper edge of the upper spherical outer surface 437. In operation, a driving tool (not shown) is received in the internal drive feature 441, being seated at the base 440 and engaging the faces 442 for both driving and rotating the shank body 406 into the vertebra 415.

The shank 404 shown in the drawings is cannulated, having a small central bore 445 extending an entire length of the shank 404 along the axis G, coaxial with the threaded body 406. The bore 445 has a first circular opening 446 at the shank tip 428 and a second circular opening 448 at the driving feature seating surface 440. The bore 445 provides a passage through the shank 404 interior for a length of wire (not shown) inserted into the vertebra 415 prior to the insertion of the shank body 406, the wire providing a guide for insertion of the shank body 406 into the vertebra 415.

Figure 21:
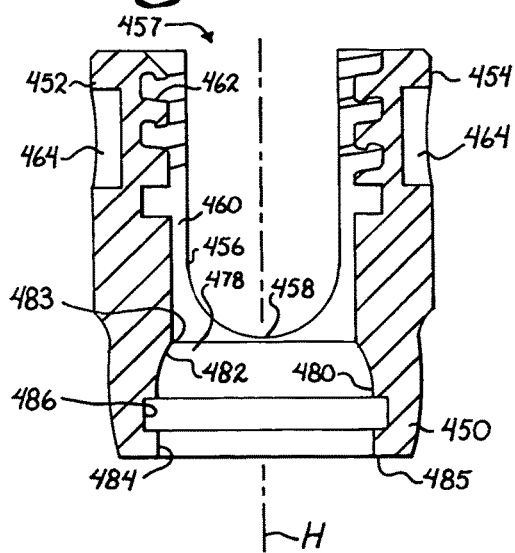
FIG. 21 is an enlarged cross-sectional view of the receiver, taken along the line 21-21 of FIG. 18.

Referring to FIGS. 21 and 25-26, the receiver 410 is substantially similar to the receivers 10 and 210 previously described herein and thus those descriptions are incorporated by reference herein with respect to the receiver 410. The receiver 410 has an axis of rotation H and further includes a receiver base 450, arms 452 and 454, a U-shaped channel 456 with an upper opening 457, a lower seat 458, an interior surface 460, guide and advancement structure 462, grip bores 464, a chamber or cavity 478, a lower inner surface 480, an upper inner spherical surface 482, a ridge 483, a lower opening 484, a base exterior 485 and a groove 486 the same or substantially similar to the respective base 50, arms 52 and 54, U-shaped channel 56 with upper opening 57, lower seat 58, interior surface 60, guide and advancement structure 62, grip bores 64, cavity 78, lower inner surface 80, upper inner spherical surface 82, ridge 83, lower opening 84, base exterior 85 and groove 86 previously described herein with respect to the receiver 10 of the assembly 1.

Although not shown, the grip bores 464 may include recesses similar to the recesses 66 described herein with respect to the assembly 1. Also at the opening 484, the surface is substantially cylindrical, having a radius sufficient to allow for the uploading of the shank upper portion 408 through the opening 484 and beyond the groove 486 and into the chamber 478 in slidable engagement with the surfaces 480 and 482, with the ridge 483 providing a stop so that the upper portion 408 is prohibited from passing through the U-shaped channel 456. As with the previously described embodiments, the lower inner surface 480 disposed above and adjacent the groove 486 may be a continuation of the spherical surface 482 as shown in FIG. 21 or in some embodiments, the lower inner surface 480 may be substantially cylindrical in form as illustrated in FIGS. 15 and 16 with respect to the assembly 201.

The receiver 410 also differs slightly from the previously described receivers 10 and 210 in outward configuration or form. For example, the base 450 is substantially cylindrical in outer form and the arms 452 and 454 include added outwardly extending material or thickness, providing the same basic functions as the bases and arms of the receivers 10 and 210, but advantageously reducing bulk where not necessary at the base, and adding bulk, and thus strength, at the arms 452 and 454.

Figure 18:
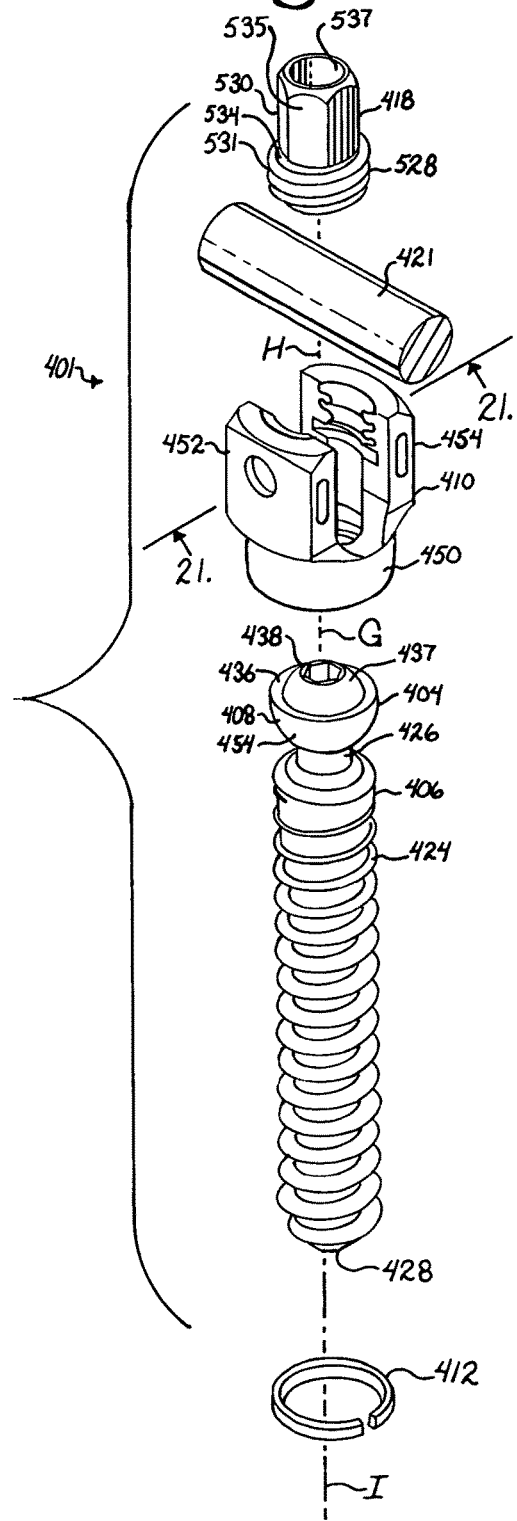
FIG. 18 is an exploded perspective view of a third embodiment of a polyaxial bone screw assembly according to the present invention having a shank, a receiver, and a retaining structure, and shown with a rod and a closure structure.
Figure 19:
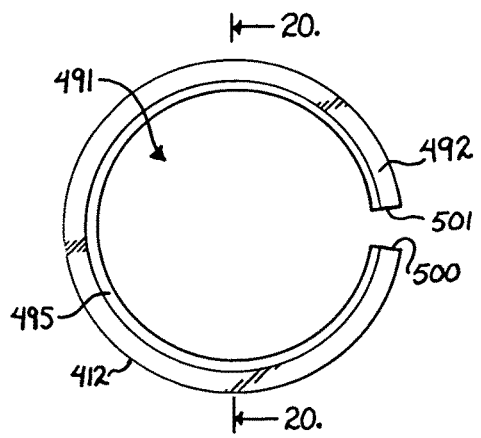
FIG. 19 is an enlarged top plan view of the retaining structure of FIG. 18.
Figure 20:
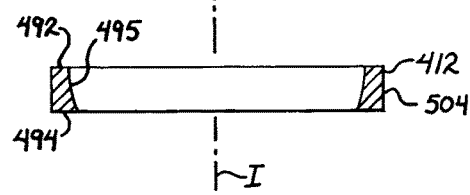
FIG. 20 is a cross-sectional view taken along the line 20-20 of FIG. 19.

The retaining structure or collar 412 that is used to retain the capture structure 408 of the shank 404 within the receiver 410 is best illustrated in FIGS. 18-20. The structure 412 has a central axis I that is operationally the same as the axis H associated with the receiver 410 when the capture structure 408 and the retaining structure 412 are installed within the receiver 410. The retaining structure 412 is the same or substantially similar to the retaining structure 12 previously described herein and thus the description of the structure 12 is incorporated by reference herein with respect to the structure 412. Specifically, the structure 412 includes a central channel 491, a top 492, a bottom 494, a substantially spherical inner surface 495, end surfaces 500 and 501 and an outer cylindrical surface 504, the same or substantially similar to respective central channel 91, top 92, bottom 94, spherical inner surface 95, end surfaces 100 and 101 and outer cylindrical surface 104 of the retaining structure 12. Unlike the structure 12, the structure 412 does not include a lower inner chamfer. The entire inner surface of the structure 412 is substantially spherical. However, it is foreseen that the structure 412 may include such a sloping or conical chamfer or bevel.

Similar to what has been previously described herein with respect to the width X of the structure 12 and the width between surfaces 300 and 301 of the structure 212, a width or space between the surfaces 500 and 501 is determined by a desired amount of compressibility of the open retaining structure 512 when loaded into the receiver 510. The space or distance between the surfaces 500 and 501 shown in FIG. 19 provides adequate space between the surfaces 500 and 501 for the retaining structure 412 to be pinched, with the surfaces 500 and 501 compressed toward one another to an almost touching or touching configuration, to an extent that the compressed retaining structure 412 is up or bottom loadable through the opening 484. After passing through the opening 484 and along a portion of the cylindrical inner surface, the retaining structure 412 expands or springs back to an original uncompressed, rounded or collar-like configuration once in the groove 486. FIGS. 25 and 26 illustrate the structure 412 in a fully installed position in the receiver 410 and having an articulating or swiveling relationship with the lower spherical portion 434 of the bone screw shank 404.

The elongate rod or longitudinal member 421 that is utilized with the assembly 401 can be any of a variety of implants utilized in reconstructive spinal surgery, but is normally a cylindrical elongate structure having a smooth cylindrical surface 516 of uniform diameter. The rod 421 is the same or substantially similar to the rods 21 and 221 previously described herein. With reference to FIGS. 25 and 26, the rod 421 directly or abutingly engages the upper portion 408 of the shank 404 either at the top 438, the circular edge 443 or the upper spherical surface 437, and is biased against the upper portion 408, consequently biasing the shank 404 downwardly in a direction toward the base 450 of the receiver 410 when the assembly 401 is fully assembled. For this to occur, the shank upper portion 408 must extend at least slightly into the space of the channel 456 when engaging the retaining structure 412. The shank 404 is thereby locked or held in position relative to the receiver 410 by the rod 421 firmly pushing downward on the shank upper portion 408.

With reference to FIGS. 18 and 25-27, the closure structure or closure top 418 can be any of a variety of different types of closure structures for use in conjunction with the present invention with suitable mating structure on the upstanding arms 452 and 454. In the embodiment shown, the closure top 418 is rotatably received between the spaced arms 452 and 454. It is foreseen that a mating and advancement structure could be located on the external surfaces of the arms 452 and 454 for mating with a closure top.

The illustrated closure structure 418 is substantially similar to the break-off closure structure 18 previously described herein. The structure 418 includes a base 528, a break-off head 530, a guide and advancement structure 531, a bottom surface 532 having a projection or point 533, a neck 534, and external faceted surface 535, a central bore 537 and an internal drive 540 in the base 528 substantially similar to the respective base 128, break-off head 130, guide and advancement structure 131, bottom surface 132, point 133, neck 134, external faceted surface 135, central bore 137 and internal drive 140 in the base 128 of the closure structure 18. When installed, the closure structure 418 operably biases against the rod 421 by advancement and applies pressure to the rod 421, so that the rod 421 is urged downwardly against the shank upper portion 408 that extends into the channel 456. Downward biasing of the shank upper portion 408 operably produces a frictional engagement between the rod 421 and the shank upper portion 408 and also urges the shank upper portion 408 toward the retaining structure 412 that has been loaded into the receiver 410 and expanded into the groove 486, so as to frictionally engage the lower spherical surface 434 of the shank upper portion 408 with the spherical surface 495 of the retaining structure 412 fixing the shank 404 in a selected, rigid position relative to the receiver 410. Similar to the assembly 201 previously described herein, it is noted that because the illustrated shank upper portion 408 includes the flat surface 438, circular edge 443 and spherical surface 437 and the rod 421 may engage any of such surfaces, the rod 421 may be seated at a distance from the receiver lower seat 458 and the closure structure base 528 may not be disposed flush to a top of the receiver 410 when the break-off head 530 has been broken off and the base 528 is fully engaged with the rod 421 biasing the rod 421 into locking engagement with the shank 404. Such placement of the closure structure 418 and the rod 421 does not hinder the closure structure 418 from seating in the receiver 410 and fixing the rod 421 in a locked position within the receiver 410.

In use, the assembly 401 is assembled, implanted, utilized, disassembled and removed identically or substantially similarly to what has been previously described herein with respect to the assembly 1. Therefore such discussion is incorporated by reference herein with respect to the assembly 401.

FIGS. 25 and 26 illustrate the polyaxial bone screw assembly 401 and including the rod 421 and the closure structure 418 positioned at various articulations or locked angular orientations: one in which the axis G of the bone screw shank is coaxial with the axis H of the receiver (FIG. 25); and one in which the axis G of the bone screw shank and the axis H of the receiver are not coaxial (FIG. 26). FIG. 27 also shows the shank 404 implanted in the vertebra 415. As previously described, full locking installation is obtainable when the rod 421 engages the top surface 438, the rim 443 or the upper spherical surface 437, even though such engagement places the rod 421 higher in the channel 456 and therefore the closure structure 418 does not seat in a manner that is flush with the top surface of the receiver 410.

With reference to FIGS. 28-33, the reference numeral 601 generally represents a fourth embodiment of a bone screw assembly according to the present invention. The assembly 601 includes a shank 604 having an axis of rotation J that further includes a body 606 integral with an upwardly extending upper portion or capture structure 608; a receiver 610 having an axis of rotation K; and an independent open retaining structure 612 having an axis of rotation L. The shank 604, the receiver 610 and the retaining structure 612 preferably are assembled prior to implantation of the shank body 606 into a vertebra. FIGS. 28, 32 and 33 further show a closure structure 618 for compressing and biasing a longitudinal member such as a rod 621 against the shank upper portion 608 biasing the upper portion 608 into fixed frictional contact with the retaining structure 612 installed in the receiver 610, so as to fix the rod 621 relative to the vertebra 615. The receiver 610, the retaining structure 612 and the shank 604 cooperate in such a manner that the receiver 610 and the shank 604 can be secured at any of a plurality of angles, articulations or rotational alignments relative to one another and within a selected range of angles both from side to side and from front to rear, to enable flexible or articulated engagement of the receiver 610 with the shank 604 until both are locked or fixed relative to each other near an end of an implantation procedure.

Figure 29:
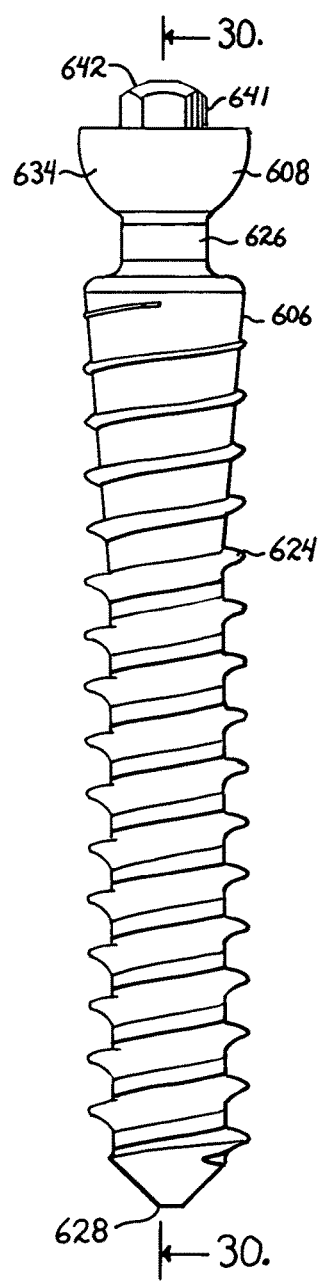
FIG. 29 is an enlarged front elevational view of the shank of FIG. 28.
Figure 30:
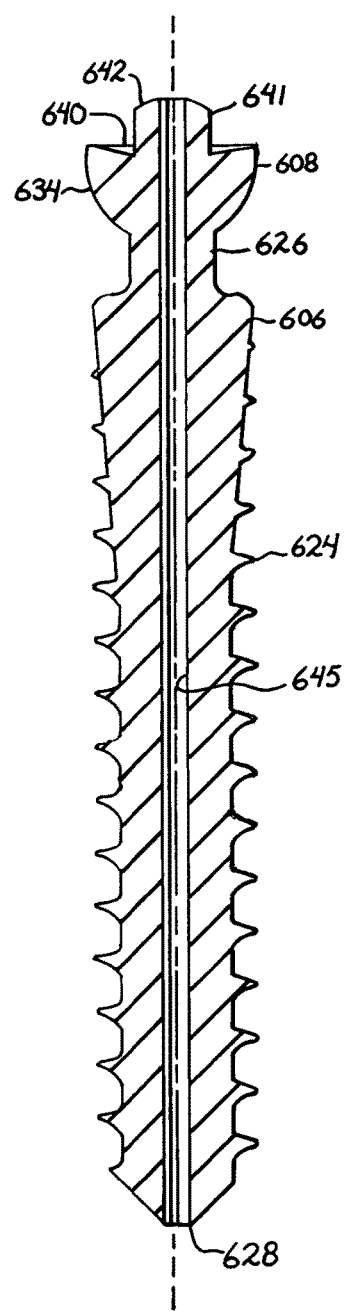
FIG. 30 is a cross-sectional view taken along the line 30-30 of FIG. 29.
Figure 31:
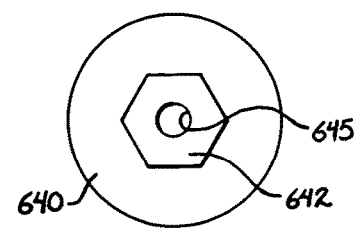
FIG. 31 is an enlarged top plan view of the shank of FIG. 29.

The shank 604, best illustrated in FIGS. 29-31, is elongate, with the shank body 606 and the upper portion 608 being substantially similar to the shank body 6 and upper portion 8 of the shank 4 previously described herein. Furthermore, the shank 605 includes a thread 624, a neck 626, a tip 628, an upper portion partially spherical surface 634, seating surface 640, a tool engagement structure 641, a top 642 and a cannulation bore 645 identical or substantially similar to the thread 24, neck 26, tip 28, upper portion spherical surface 34, seating surface 40, tool engagement structure 41, top 42 and cannulation bore 45 of the shank 4. Therefore a description of these features will not be repeated here with the exception of the seating surface 640. The shank upper portion 608 does not include an annular surface 38 cooperating with the recessed seating surface 40 described herein with respect to the shank upper portion 8. Rather, the seating surface 640 of the shank upper portion 608 extends or slopes outwardly and upwardly from the tool engagement structure 641 to the substantially spherical surface 634 as best illustrated in FIG. 30. It is noted that in smaller embodiments of bone screws according to the invention, it may be difficult to machine or otherwise form the recessed surface 38 into the bone screw upper portion 8 (illustrated in FIGS. 6 and 7). In such embodiments, the more easily formable sloping seating surface 640 provides adequate seating surface about the tool engagement structure 641 and a slightly elongated tool engagement structure 641 for rotating and implantation of the bone screw shank body 606 into a vertebra.

Referring to FIGS. 28, 32 and 33, the receiver 610 is substantially similar to the receiver 410 previously described herein with one exception, the type of helically wound guide and advancement structure for use in cooperation with the closure structure 618. Specifically, the receiver 610 includes a receiver base 650, arms 652 and 654, a U-shaped channel 656 with an upper opening 657, a lower seat 658, and an interior surface 660 identical or substantially similar to the receiver base 450, arms 452 and 454, U-shaped channel 456 with an upper opening 457, lower seat 458, and the interior surface 460 of the receiver 410. The receiver 610 includes a guide and advancement structure 662 that is located within the receiver 610 similarly to the guide and advancement structure 462 of the receiver 410. However, the guide and advancement structure 462 is a flange form while the guide and advancement structure 662 is a reverse angle form, best illustrated in FIGS. 32 and 33. The receiver 610 further includes grip bores 664, an inner chamber or cavity 678 having a spherical surface and a groove 686 that is identical or substantially similar to the respective grip bores 464, and inner chamber 678 features, including the groove 486 of the receiver 410 of the assembly 401.

The retaining structure or collar 612 that is used to retain the capture structure 608 of the shank 604 within the receiver 610 is best illustrated in FIGS. 28 and 32-33. The structure 612 is identical or substantially similar to the retaining structure 412 previously described herein.

The elongate rod or longitudinal member 621 that is utilized with the assembly 601 can be any of a variety of implants utilized in reconstructive spinal surgery, but is normally a cylindrical elongate structure having a smooth cylindrical surface 687 of uniform diameter. The rod 621 is substantially similar in form and function to the rods 21, 221 and 421 previously described herein.

With reference to FIGS. 28 and 32-33, the closure structure or closure top 618 can be any of a variety of different types of closure structures for use in conjunction with the present invention with suitable mating structure on the upstanding arms 652 and 654. In the embodiment shown, the closure top 618 is rotatably received between the spaced arms 652 and 654. It is foreseen that a mating and advancement structure could be located on the external surfaces of the arms 652 and 654 for mating with a closure top.

The illustrated closure structure 618 is substantially similar to the break-off closure structure 418 previously described herein with the exception that the structure 618 has a reverse angle helical form guide and advancement structure 691, rather than the flange form guide and advancement structure 531 of the closure structure 418.

Specifically, the structure 618 includes a base 688, a break-off head 690, a bottom surface 692 having a projection or point 693, a neck 694, and external faceted surface 695, a central bore 697 and an internal drive 698 in the base 688 substantially similar to the respective base 528, break-off head 530, bottom surface 532, point 533, neck 534, external faceted surface 535, central bore 537 and internal drive 540 in the base 528 of the closure structure 418.

When installed, the closure structure 618 operably biases against the rod 621 by advancement and applies pressure to the rod 621, so that the rod 621 is urged downwardly against the shank upper portion 608 that extends into the channel 656. Downward biasing of the shank upper portion 608 operably produces a frictional engagement between the rod 621 and the shank upper portion 608 and also urges the shank upper portion 608 toward the retaining structure 612 that has been loaded into the receiver 610 and expanded into the groove 686, so as to frictionally engage the spherical surface 634 of the shank upper portion 608 with the inner spherical surface of the retaining structure 612 fixing the shank 604 in a selected, rigid position relative to the receiver 610.

In use, the assembly 601 is assembled, implanted, utilized, disassembled and removed identically or substantially similarly to what has been previously described herein with respect to the assembly 1. Therefore such discussion is incorporated by reference herein with respect to the assembly 601.

FIGS. 32 and 33 illustrate the polyaxial bone screw assembly 601 and including the rod 621 and the closure structure 618 positioned at various articulations or locked angular orientations: one in which the axis J of the bone screw shank is coaxial with the axis K of the receiver (FIG. 32); and one in which the axis J of the bone screw shank and the axis K of the receiver are not coaxial (FIG. 33).

Figure 34:
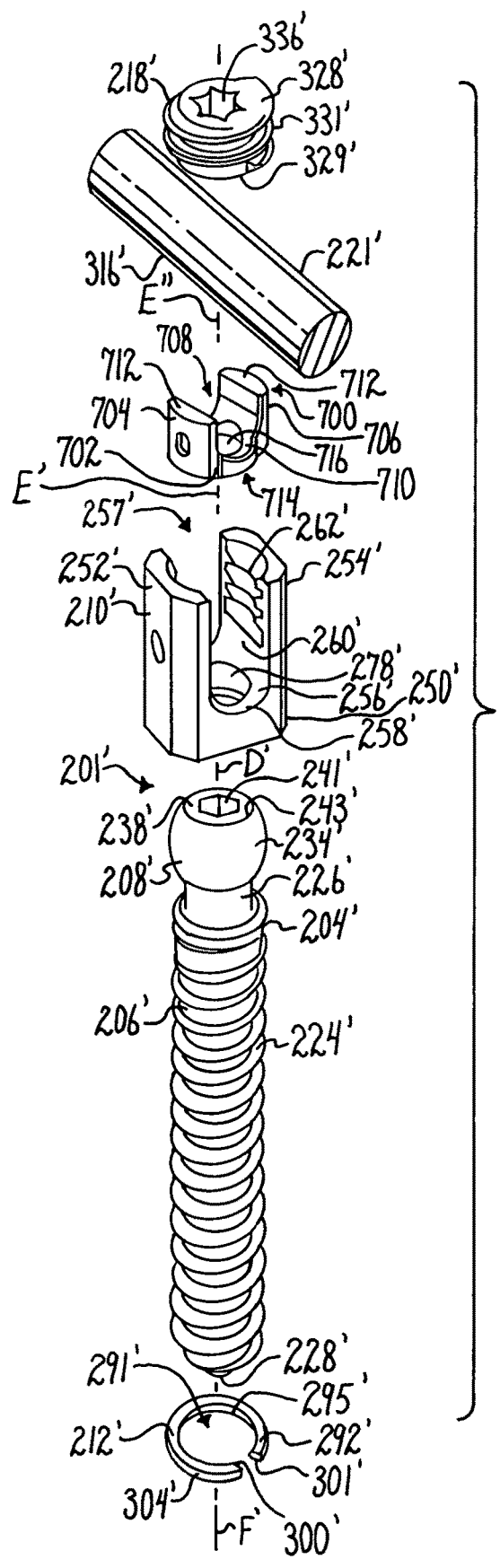
FIG. 34 is an exploded perspective view of another embodiment of a polyaxial bone screw assembly according to the present invention having a shank, a receiver, a retaining structure, and a compression transfer member, and shown with a rod and a closure structure.
Figure 35:
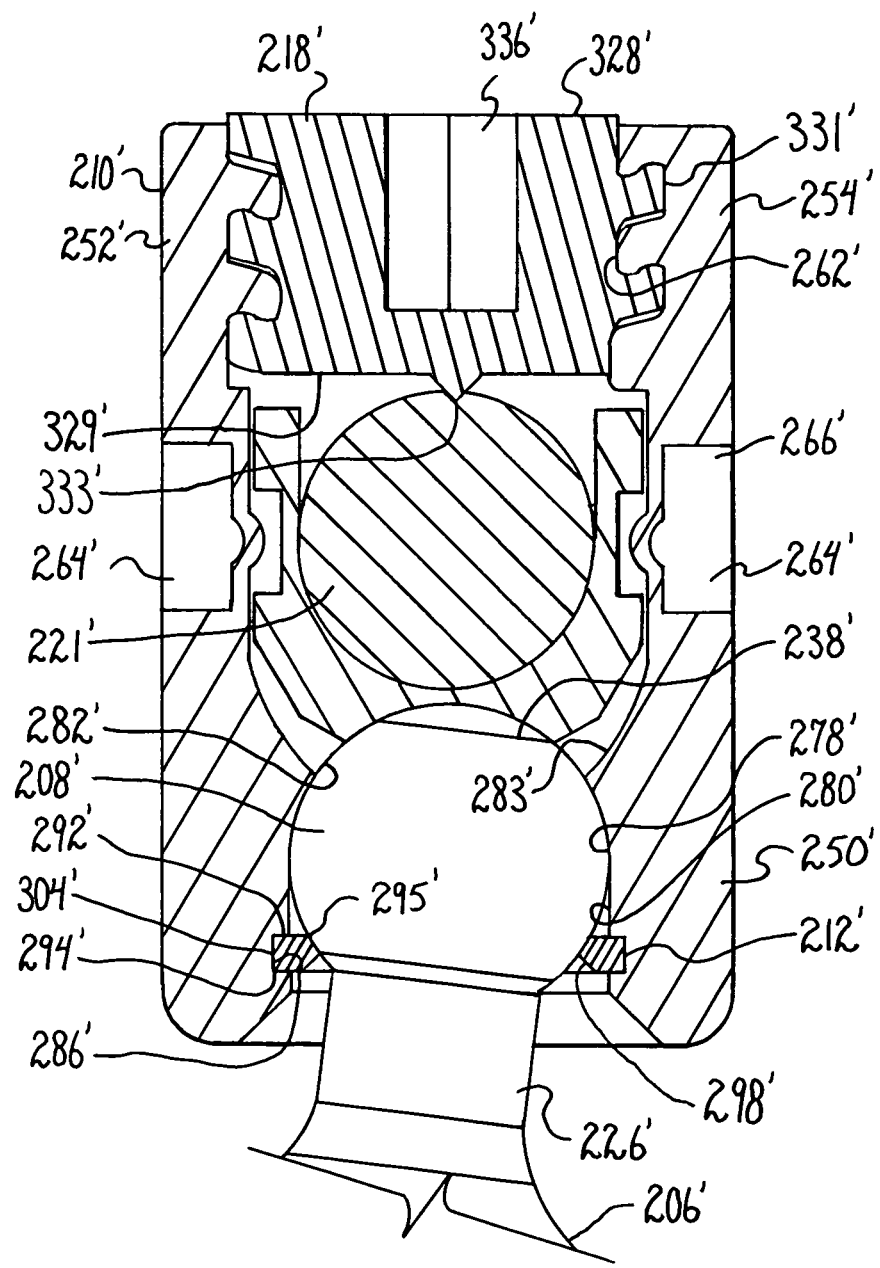
FIG. 35 is an enlarged partial front elevational view of the shank of FIG. 34 shown fully assembled with the retaining structure, receiver, compression transfer member, rod and closure structure of FIG. 34, with portions broken away to show the detail thereof.

FIGS. 34-35 illustrate an alternative embodiment of a polyaxial bone screw assembly 201' of the present invention, which is similar to that of assembly 201 (FIG. 11), with the exception of inclusion of a compression insert 700. Thus, the description of the assembly 201 is incorporated by reference with respect to the assembly 201'. Specifically, the assembly 201' includes a shank 204', a receiver 210', an independent open retaining structure 212', and a compression insert 700. In FIG. 34, the assembly 201' is shown with a rod 221' (e.g., elongated member) and a closure structure 218'. Preferably, the shank 204', receiver 210', retaining structure 212', and compression insert 700 are assembled prior to implantation of the shank body 206' into a vertebra 215.

The shank 204' is substantially similar to the shank 204 previously described herein, and includes an upper portion 208' with a capture structure having an outer convex substantially spherical first surface 234' that extends upwardly and terminates in a substantially planar annular surface 238'. The surface 234' has an outer radius configured for sliding cooperation and ultimate frictional mating with a concave surface of the retaining structure 212' and a substantially spherical inner surface of the receiver 210' that has a substantially similar radius, as discussed elsewhere herein. The planar annular surface 238' is substantially perpendicular to the longitudinal axis D' of the shank 204' and includes a countersunk tool engagement formation 241' (e.g., internal drive feature or imprint) coaxial with axis D'.

The receiver 210' has an axis of rotation E' and is substantially similar to the receiver 210 previously described herein. The receiver 210' includes a receiver base 250', arms 252' and 254', a U-shaped channel 256' (e.g., elongate member-receiving channel) with an upper opening 257', a lower seat 258', an interior surface 260', guide and advancement structure 262', grip bores 264', recesses 266', a chamber or cavity 278', a lower inner surface 280', an inner spherical surface 282' (e.g., concave partially spherically shaped second surface), a ridge 283', a lower opening 284', a base exterior 285' and a groove 286' the same or substantially similar to those of receivers 10 and 210. The chamber 278' communicates with the U-shaped channel 256' via an opening located at the ridge 283'. The shank 204' upper portion 208' is received (e.g., uploaded) in the cavity 278' through the lower opening 284'.

The retaining structure or collar 212', which is substantially similar to the retaining structure 212, is received in the receiver cavity 278' and secured to the receiver 210' in a fixed relation thereto, when the shank upper portion 208' is in the receiver 210' (FIGS. 34-35). The structure 212' has a central axis F', which is operationally the same as the axis E' associated with the receiver 210' when the capture structure 208' and the retaining structure 212' are installed within the receiver 210'. The retaining structure 212' is the same or substantially similar to the retaining structure 212 described herein, the description of which is incorporated by reference herein with respect to the structure 212'. Specifically, the retaining structure 212' includes a partially spherical inner surface 295' (e.g., third surface) that is sized and shaped to receive a portion of the outer convex substantially spherical first surface 234' of the shank 204'.

The retaining structure 212' is sized and shaped to retain the shank upper portion 208' within the receiver cavity 278', such as described herein. For example, as shown in FIG. 35, the shank upper portion 208' is sized and shaped to extend above the retaining structure 212', such as via neck 226'. When the shank upper portion 208' is retained in the cavity 278' by the retaining structure 212', the shank upper portion 208' receives downward force from a rod 221' positioned in the channel 256', so as to lock the angular position of the receiver 210' relative to the shank 204' in a locked position. Further, the assembly 201' includes an unlocked position wherein the shank upper portion 208' is in sliding, pivotable relation with the retaining structure 212' and a locked position wherein the shank first surface 234' is simultaneously in direct frictional engagement with the receiver second surface 282' and the retaining structure third surface 295'. Stated another way, the second surface 282' of the receiver 210' and the third surface 295' of the retainer 212' cooperate to receive (e.g., frictionally engage) the first surface 234' of the shank capture structure 208' to allow polyaxial rotation of the shank 204' relative to the receiver 210' in the unlocked configuration during implantation. Thus, when the assembly 201' is in an unlocked position, the first surface 234' of the shank upper portion 208' slidably matingly engages the second surface 282' of the receiver cavity 278'.

Referring to FIGS. 34-35, the assembly 201' includes a compression transfer member 700 (e.g., pressure insert, compression insert, spacer) received in the receiver 210' above the cavity 278', and includes a substantially cylindrical body 702 and a pair of upstanding spaced apart arms 704 and 706 forming a through-channel 708 (e.g., an elongate member (e.g., rod 221') receiving channel), such as described in greater detail in U.S. Application No. 61/268,708, filed Jun. 15, 2009 and entitled "Dynamic Stabilization Assembly with Cord and Flush Sliding Sleeves," which is incorporated herein by reference in its entirety. In some embodiments, the insert 700 and receiver 210' are sized and shaped such that the insert 700 is installed in and secured to the receiver 210' via a "twist-and-lock" mechanism, such as described in U.S. Ser. No. 61/268,708. For example, with reference to FIGS. 36 and 37 (corresponding to FIGS. 35 and 36 of U.S. Application No. 61/268,708), a receiver 807 includes a pair of upstanding arms 834 and 835. A chamber or cavity 847 is located within the receiver base that opens upwardly into a U-shaped channel 838. An upper portion of the cavity 847 includes a substantially cylindrical surface that extends upward through the channel 838 to include a run-out surface 853 located directly beneath a guide and advancement structure 842. Formed in the run-out surface 853 under the guide and advancement structure 842 of both of the arms 834 and 835 is a recess 854 partially defined by a stop or abutment wall 855. A cooperating compression insert 809 includes a protruding structure 894 on each arm thereof that abuts against the respective wall 855 of each of the receiver arms, providing a centering stop when the insert 809 is rotated into place.

The lower compression or pressure insert 809 includes a substantially cylindrical body 870 integral with a pair of upstanding arms 872. The body 870 and arms 872 of the insert 809 form a generally U-shaped, open, through-channel 874. The arms 872 disposed on either side of the channel 874 extend outwardly from the body 870. The arms 872 are sized and configured for placement near the cylindrical run-out surface 853 below the guide and advancement structure 842 at the receiver inner arms 834 and 835. Each of the arms 872 includes a top surface 878 that is ultimately located directly beneath the guide and advancement structure 842. Each arm 872 further includes a partially cylindrical outer surface 880 sized and shaped to fit within the receiver 807 at cylindrical run-out relief or surface 853 located below the guide and advancement structure 842. Each of the outer surfaces 880 further includes a recess 882 sized and shaped to receive holding tabs or crimped material from the receiver 807. The recesses 882 are preferably oval or elongate such that some desirable upward and downward movement of the insert 809 along the axis B' of the receiver 807 is not prohibited. Each of the arms 872 of the compression insert 809 include the protruding structure 894 located on opposite sides of the arms such that when the insert 809 is dropped down into the receiver 807 as shown by the arrow M in FIG. 36 and then rotated into place in a clockwise direction as shown by the arrow N in FIG. 37, the structure 894 abuts the wall 855 of the recessed area 854 when the insert is in a desired centered location within the receiver, with the apertures 882 in alignment with tool engaging apertures 844 formed on the outsides of the arms 834 and 835 of the receiver.

Figure 36:
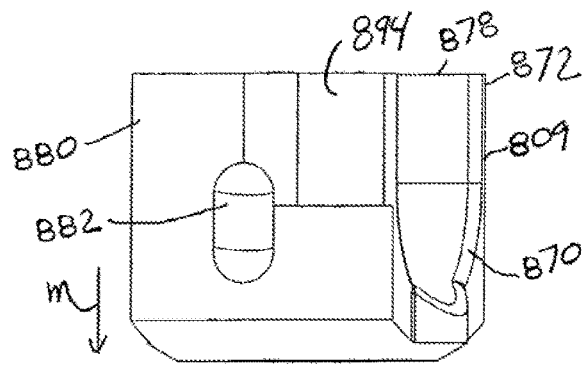
FIG. 36 is an enlarged and partial perspective exploded view of the receiver and compression insert of another embodiment of the polyaxial bone screw assembly of FIG. 34, shown in an initial stage of assembly.
Figure 37:
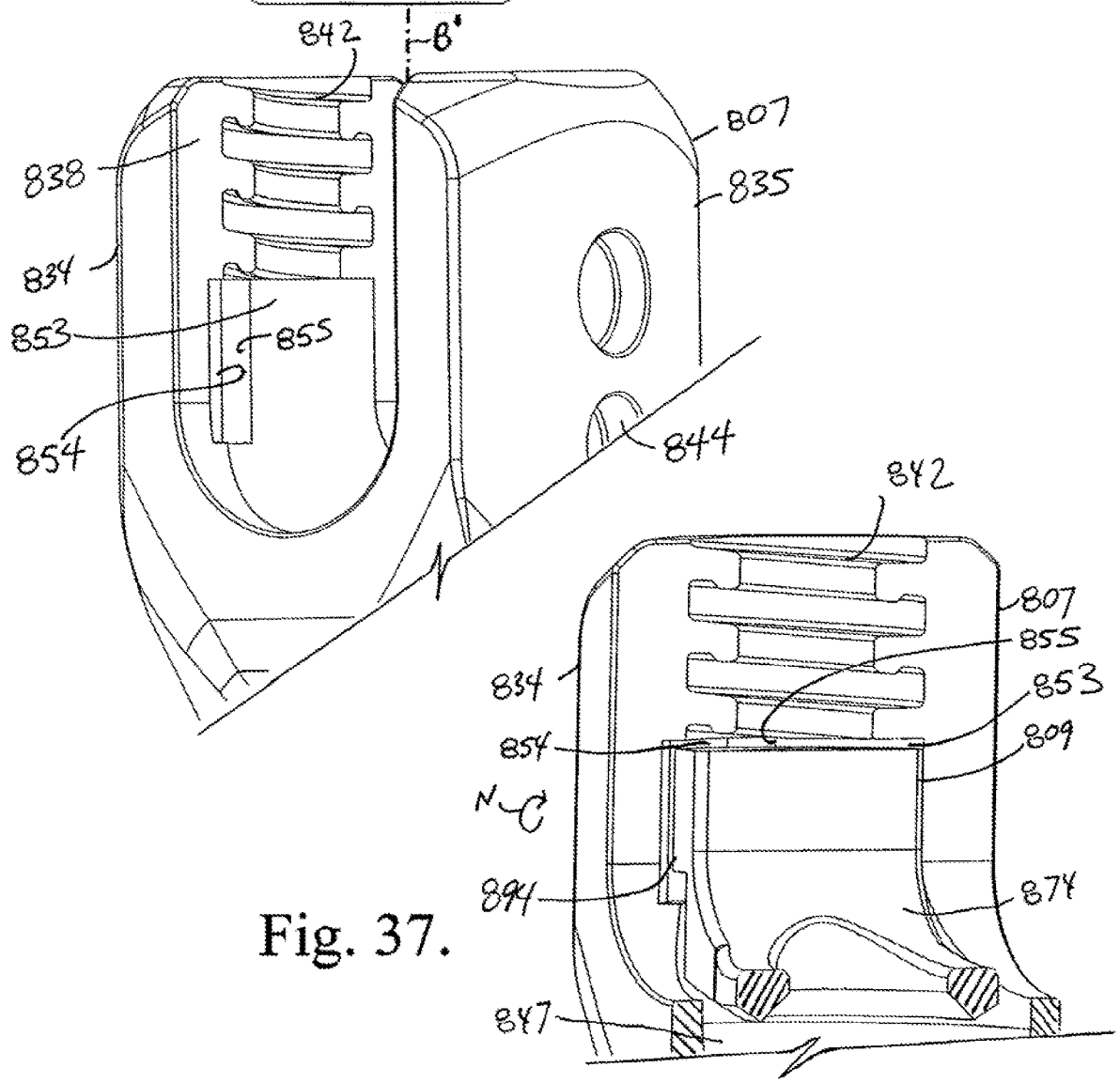
FIG. 37 is an enlarged and partial perspective view of the receiver and compression insert of FIG. 36 with portion broken away to show the detail thereof and shown in a later stage of assembly.

The pressure inset body 870 located between the arms 872 has an outer diameter slightly smaller than a diameter between crests of the guide and advancement structure 842 of the receiver 807, allowing for top loading of the compression insert 809 into the receiver 807 through the U-shaped channel 838, with the arms 872 of the insert 809 being located between the arms 834 and 835 of the receiver during insertion of the insert 809 into the receiver 807 (see FIG. 36). Once located between the guide and advancement structure 842 and a shank upper portion, the insert 809 is rotated into place about the axis B' until the arms 872 of the insert are directly below the guide and advancement structure 842 at or near the run-out surface 853 and the protruding structure 894 abuts against the wall 855 of the recess 854. The lower compression insert 809 is sized such that the insert 809 is ultimately received within the cylindrical surface of the receiver 807 below the guide and advancement structure 842. The receiver 807 fully receives the lower compression insert 809 and blocks the structure 809 from spreading or splaying in any direction.

With reference back to FIGS. 34-35, in other embodiments, the insert 700 is placed in the receiver 210' and secured by alternative fastening systems known in the art, such as but not limited to crimping, welding or an adhesive. In some embodiments, the insert 700 is movably secured within the receiver 210' until such time that the assembly 201' is installed and the insert 700 is locked in place within the receiver 210' via insertion of a rod 221' and closure 218' into the receiver 210' and biasing the closure 218' against the rod 221', which in turn is biased against the inert 700.

Figure 38:
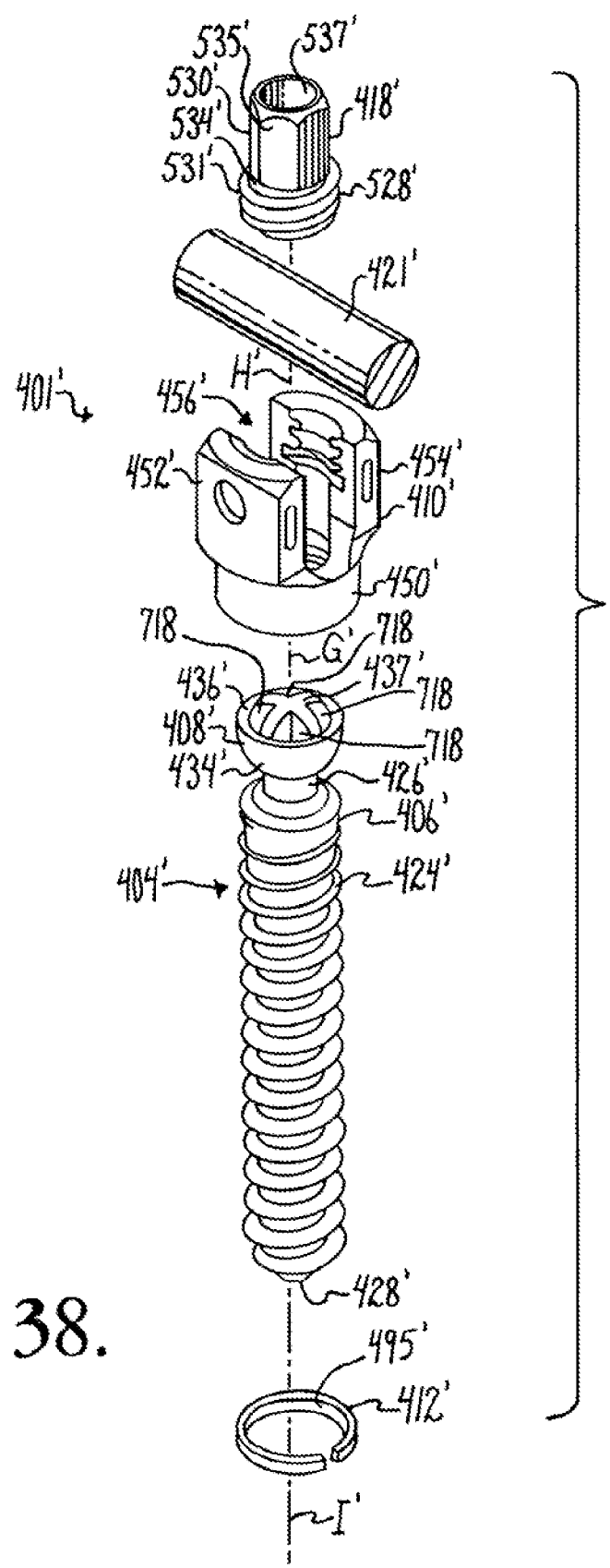
FIG. 38 is an exploded perspective view of yet another embodiment of a polyaxial bone screw assembly according to the present invention having a shank, the shank upper portion including a plurality of pie slide-shaped apertures, a receiver, and a retaining structure, and shown with a rod and a closure structure.

FIG. 38 illustrates yet another embodiment of a bone screw assembly 401', which is substantially similar to the assembly 401 described with reference to FIGS. 18-27, with the exception of the tool engagement formation described below. The description of assembly 401 is incorporated herein by reference. The polyaxial bone screw assembly 401' includes a bone screw shank 404', a receiver 410' and a retainer 412'. The shank upper portion 408' (e.g., capture structure) is sized and shaped for uploading into the receiver 410' and includes an outer, lower convex hemispherical first surface 434' and a convex hemispherical upper surface 437'. As shown in FIG. 38, the hemispherical first surface 434' extends outwardly and upwardly and terminates in a substantially planar annular surface 436'. The hemispherical upper surface 437' is generally dome-shaped and extends upwardly from the planar annular surface. It is noted that the diameter of the hemispherical first surface 434' is greater than the diameter of the hemispherical upper surface 437'. Further, when assembled, the hemispherical upper surface 437' extends into the rod-receiving channel 456' in the receiver 410' to directly engage a rod 421' or other elongate member in the rod-receiving channel 456'.

The hemispherical upper surface 437' includes a countersunk tool engagement formation that includes a plurality of apertures 718, and thus is adapted for non-slip engagement by a tool for driving the bone screw shank 404' into bone. In some embodiments, the tool engagement formation includes at least two axially-offset, spaced apart apertures 718 having a profile selected from the group consisting of circles, polygons, multi-lobular stars, pie slices and combinations thereof. In the embodiment shown in FIG. 38, the tool engagement formation includes four equally spaced apart apertures 718, wherein each aperture 718 has a pie slice-shaped profile. Accordingly, in this embodiment, the tool engagement formation is engaged by a tool having four pie slice-shaped fingers that are removably inserted into the apertures 718, such that the shank 404' can be driven into a vertebra 215.

As discussed elsewhere herein, the receiver 410' is substantially similar to the structure 410, and includes a pair of arms 452', 454' that form a rod-receiving channel 456'. Like the structure 410, the receiver 410' includes a cavity (e.g., similar to cavity 480) with a concave partially spherically shaped second surface (e.g., similar to surface 482) and an opening to an exterior of the receiver opposite the pair of arms, the cavity communicating with the channel 456', such that the bone screw upper portion 408' is received in the cavity through the opening.

As discussed elsewhere herein, the retaining structure 412' is substantially similar to the structure 412, and receivable in the cavity and securable to the receiver 410' in fixed relation thereto when the shank upper portion 408' is in the receiver 410'. The retaining structure 412' includes a third surface 495' sized and shaped to receive a portion of the shank first surface 434', such as described with reference to structure 401. Further, in this embodiment, the receiver second surface 482' and the retainer third surface 495' cooperatingly receive the first surface 434' of the shank capture structure 408' to allow polyaxial rotation of the shank 406' relative to the receiver 410' in the unlocked configuration during assembly. Stated another way, the first surface 434' slidably matingly engages the second surface 482' (e.g., and the third surface 495') in the unlocked position.

It is to be understood that while certain forms of the present invention have been illustrated and described herein, it is not to be limited to the specific forms or arrangement of parts described and shown.

What is claimed and desired to be secured by Letters Patent is as follows:

1. A pivotal bone anchor assembly for a securing a cylindrically-shaped elongate rod to a bone of a patient via a closure, the pivotal bone anchor assembly comprising:
   a receiver comprising a longitudinal axis of rotation, an upper portion defining an open first channel configured to receive the elongate rod, and a base defining a cavity communicating with the first channel and with a bottom surface of the receiver through a bottom opening, the first channel having a discontinuous closure mating structure formed therein, the receiver including a substantially cylindrical interior surface extending downward below the closure mating structure with an internal abutment surface formed therein, and the cavity further defined by an interior seating surface adjacent the bottom opening;
   a shank comprising a capture portion with a partial spherical surface and a central drive tool-engaging structure formed therein, and an anchor portion opposite the capture portion configured for fixation to the bone, the capture portion being positionable within the cavity of the receiver with the shank extending downward through the bottom opening;
   a retainer configured for positioning within the cavity of the receiver so as to capture and hold the capture portion within the cavity, with an outer surface of the retainer engaged against the interior seating surface of the cavity while allowing for pivotal movement between the receiver and the shank; and
   a pressure insert configured for top loading into the receiver separate and apart from the shank, the pressure insert having a central opening centered on the longitudinal axis of rotation of the receiver configured for a drive tool to pass through to engage the drive tool-engaging structure of the shank, outer side surfaces having alignment notches formed therein and protruding surfaces adjacent the alignment notches, and a partially-cylindrical upward-facing curved surface entirely surrounding the central opening to define a second channel extending between the outer side surfaces and sized and shaped to receive the cylindrically-shaped elongate rod, the pressure insert being top loaded into a first position within the substantially cylindrical interior surface portion of the receiver with the second channel of the pressure insert in a non-alignment orientation with respect to the first channel,
   wherein after being top loaded into the first position within the substantially cylindrical interior surface portion of the receiver, the pressure insert is rotatable about the longitudinal axis of rotation of the receiver, with the outer side surfaces of the pressure insert rotating below the discontinuous closure mating structure of the channel, until the protruding surfaces of the pressure insert abut the abutment surface in the substantially cylindrical interior surface to inhibit further rotation of the pressure insert within the receiver and to define a second position in which the second channel is in alignment with the first channel.

2. The pivotal bone anchor assembly of claim 1, wherein the receiver includes outer sidewall crimp holes with thin inner walls configured to deform and engage the alignment notches of the pressure insert to hold the second channel in alignment with respect to the first channel.

3. The pivotal bone anchor assembly of claim 1, wherein the pressure insert is top loadable into the receiver prior to the shank.

4. The pivotal bone anchor assembly of claim 1, wherein the capture portion of the shank is bottom loadable into the cavity of the receiver through the bottom opening.

5. The pivotal bone anchor assembly of claim 1, wherein the pressure insert further comprises upright arms defining an upper portion of the second channel and having top surfaces that remain spaced from the closure when the closure is used to lock the elongate rod within the pivotal bone anchor assembly.

6. The pivotal bone anchor assembly of claim 5, wherein the pressure insert upright arm top surfaces are planar.

7. The pivotal bone anchor assembly of claim 1, wherein the pressure insert further comprises upright arms defining an upper portion of the second channel and having top surfaces that engage the closure when the closure is used to lock the elongate rod within the bone anchor assembly.

8. The pivotal bone anchor assembly of claim 1, wherein the pressure insert further includes an at least partial spherical lower surface configured to engage the partial spherical surface of the capture portion of the shank.

9. The pivotal bone anchor assembly of claim 1, wherein the pressure insert further comprises upright arms defining an upper portion of the second channel, and wherein the alignment notches and protruding surfaces adjacent the alignment notches are formed into outer side surfaces of the upright arms.

10. The pivotal bone anchor assembly of claim 1, wherein the discontinuous closure mating structure is a discontinuous helically wound thread.

11. The pivotal bone anchor assembly of claim 1, wherein the retainer is configured to engage the spherical surface of the capture portion of the shank within the cavity of the receiver.

12. The pivotal bone anchor assembly of claim 1, wherein the interior seating surface of the cavity further comprises a recess configured for receiving and retaining the retainer within the cavity in a non-pivotal relation.

13. The pivotal bone anchor assembly of claim 12, wherein the recess of the cavity is a circumferential groove.

14. The pivotal bone anchor assembly of claim 1, wherein the retainer includes a partially spherical inner surface having substantially a same radius as that of the partial spherical surface of the capture portion of the shank.

15. The pivotal bone anchor assembly of claim 14, wherein the retainer includes a chamfer or beveled non-radiused surface extending from the partially spherical inner surface down to a bottom of the retainer.

16. The pivotal bone anchor assembly of claim 1, wherein the retainer is uploadable into the cavity of the receiver through the bottom opening.

17. The pivotal bone anchor assembly of claim 1, wherein the retainer further comprises first and second spaced ends, the retainer being compressible and expandable with the first and second ends being movable toward and away from one another.

18. The pivotal bone anchor assembly of claim 17, wherein the retainer is a split ring.

19. The pivotal bone anchor assembly of claim 17, wherein the first and second spaced apart opposed ends have surfaces that are obliquely oriented with respect to each other.

20. The pivotal bone anchor assembly of claim 1, wherein the spherical surface of the capture portion of the shank extends above the retainer to engage a lower surface on the pressure insert.

21. The pivotal bone anchor assembly of claim 1, wherein the central drive-tool engaging structure of the capture portion of the shank is adapted for non-slip engagement by the drive tool for driving the shank into the bone.

22. The pivotal bone anchor assembly of claim 1, wherein the shank is cannulated with a central opening extending through an entire length thereof.

23. The pivotal bone anchor assembly of claim 1, wherein the capture portion of the shank is positionable within the cavity of the receiver prior to the pressure insert.

24. A pivotal bone anchor assembly for a securing an elongate rod having a cylindrical shape to a bone of a patient, the pivotal bone anchor assembly comprising:
   a receiver comprising a longitudinal axis of rotation, an upper portion defining an open first channel configured to receive the elongate rod, and a base defining a cavity communicating with the first channel and with a bottom surface of the receiver through a bottom opening, the first channel having a discontinuous closure mating structure formed therein, the receiver including a substantially cylindrical interior surface extending downward below the closure mating structure with opposed abutment surfaces formed therein, and the cavity further defined by an interior seating surface adjacent the bottom opening;
   a shank comprising a capture portion with a partial spherical surface and a central drive tool-engaging structure formed therein, and an anchor portion opposite the capture portion configured for fixation to the bone, the capture portion of the shank being positionable within the cavity of the receiver with the shank extending downward through the bottom opening;
   a retainer configured to be positioned in the cavity of the receiver so as to capture and hold the capture portion within the cavity, with an outer surface of the retainer engaged against the interior seating surface of the cavity while allowing for pivotal movement between the receiver and the shank; and
   a pressure insert configured to be top loaded into the receiver separate and apart from the shank, the pressure insert having a central opening centered on the longitudinal axis of rotation of the receiver configured for a drive tool to pass through to engage the drive tool-engaging structure of the shank, outer side surfaces having a pair of opposite alignment notches formed therein and a pair of opposite protruding surfaces adjacent the alignment notches, and a partially-cylindrical upward-facing curved surface entirely surrounding the central opening of the pressure insert to define a second channel configured to receive the elongate rod,
   wherein the pressure insert is configured to be top loaded into a first position within the substantially cylindrical interior surface portion of the receiver with the second channel being in a non-alignment orientation with respect to the first channel, after which the pressure insert is rotatable about the longitudinal axis of rotation of the receiver, with the outer side surfaces of the pressure insert rotating below the discontinuous closure mating structure of the channel and with the second channel entering into alignment with the first channel, until the pair of opposite protruding surfaces of the pressure insert abut the opposed abutment surfaces of the substantially cylindrical interior surface to inhibit further rotation of the pressure insert within the receiver and to define a second position with the second channel being aligned with the first channel.

25. The pivotal bone anchor assembly of claim 24, wherein the retainer is configured to be resiliently compressed during uploading into the cavity of the receiver through the bottom opening.

26. The pivotal bone anchor assembly of claim 24, wherein the capture portion of the shank is configured for bottom loading into the cavity of the receiver through the bottom opening.

27. The pivotal bone anchor assembly of claim 26, wherein the shank is configured for first implantation of the anchor portion into the bone followed by assembly of the capture portion with the receiver.

* * * * *